(12) United States Patent
Wong et al.

(10) Patent No.: US 12,208,274 B2
(45) Date of Patent: Jan. 28, 2025

(54) ELECTRODE CONNECTOR

(71) Applicant: Physio-Control, Inc., Redmond, WA (US)

(72) Inventors: Jeremy Wong, Redmond, WA (US); Ryan Peter Bowman, Richland, WA (US); Zack Pahlman, Lake Forest Park, WA (US)

(73) Assignee: Physio-Control, Inc., Redmond, WA (US)

( * ) Notice: Subject to any disclaimer, the term of this patent is extended or adjusted under 35 U.S.C. 154(b) by 1129 days.

(21) Appl. No.: 17/081,910

(22) Filed: Oct. 27, 2020

(65) Prior Publication Data

US 2021/0146147 A1 May 20, 2021

Related U.S. Application Data

(60) Provisional application No. 62/937,632, filed on Nov. 19, 2019.

(51) Int. Cl.
| | | |
|---|---|---|
| *A61N 1/39* | (2006.01) | |
| *A61N 1/04* | (2006.01) | |
| *H01R 13/52* | (2006.01) | |
| *H01R 13/64* | (2006.01) | |

(52) U.S. Cl.
CPC ........... *A61N 1/3968* (2013.01); *A61N 1/046* (2013.01); *H01R 13/5224* (2013.01); *H01R 13/64* (2013.01); *H01R 2201/12* (2013.01)

(58) Field of Classification Search
None
See application file for complete search history.

(56) References Cited

U.S. PATENT DOCUMENTS 6,961,611 B2 * 11/2005 Dupelle ............... A61N 1/3968
607/5
9,916,436 B2 * 3/2018 Bielstein ............... A61N 1/3925

* cited by examiner

*Primary Examiner* — Ross N Gushi
(74) *Attorney, Agent, or Firm* — Lee & Hayes, P.C.

(57) ABSTRACT

Systems to confirm authenticity of electrodes and to provide compatibility between a medical device and associated electrodes are described. The systems include an electrode connector that stores an authentication code that is accessible to the medical device when the electrode connector is coupled to the medical device. The medical device uses the authentication code to determine an authenticity of the coupled electrodes. The electrode connector also includes physical features of a housing that allow the electrode connector to couple to different versions (e.g., older and new models) of the type of medical device. This feature allows reverse compatibility of the electrode connector to different versions of medical devices.

20 Claims, 9 Drawing Sheets

ELECTRODE CONNECTOR

CROSS-REFERENCE TO RELATED APPLICATION

This application claims the benefit of U.S. Provisional Application No. 62/937,632, titled "Electrode Connector" and filed on Nov. 19, 2019, and which is incorporated by reference herein in its entirety.

BACKGROUND

A defibrillator is a medical device configured to administer defibrillation therapy to a patient through electrodes. Typically, a defibrillator is configured to operate with device-compatible electrodes that have known properties, characteristics, or tolerances. Operating the defibrillator with electrodes from, for example, a different model or manufacturer, can reduce the effectiveness of defibrillation therapy, compromising the safety of the patient. The disclosure made herein is presented with respect to these and other considerations.

DETAILED DESCRIPTION

Figure 1:
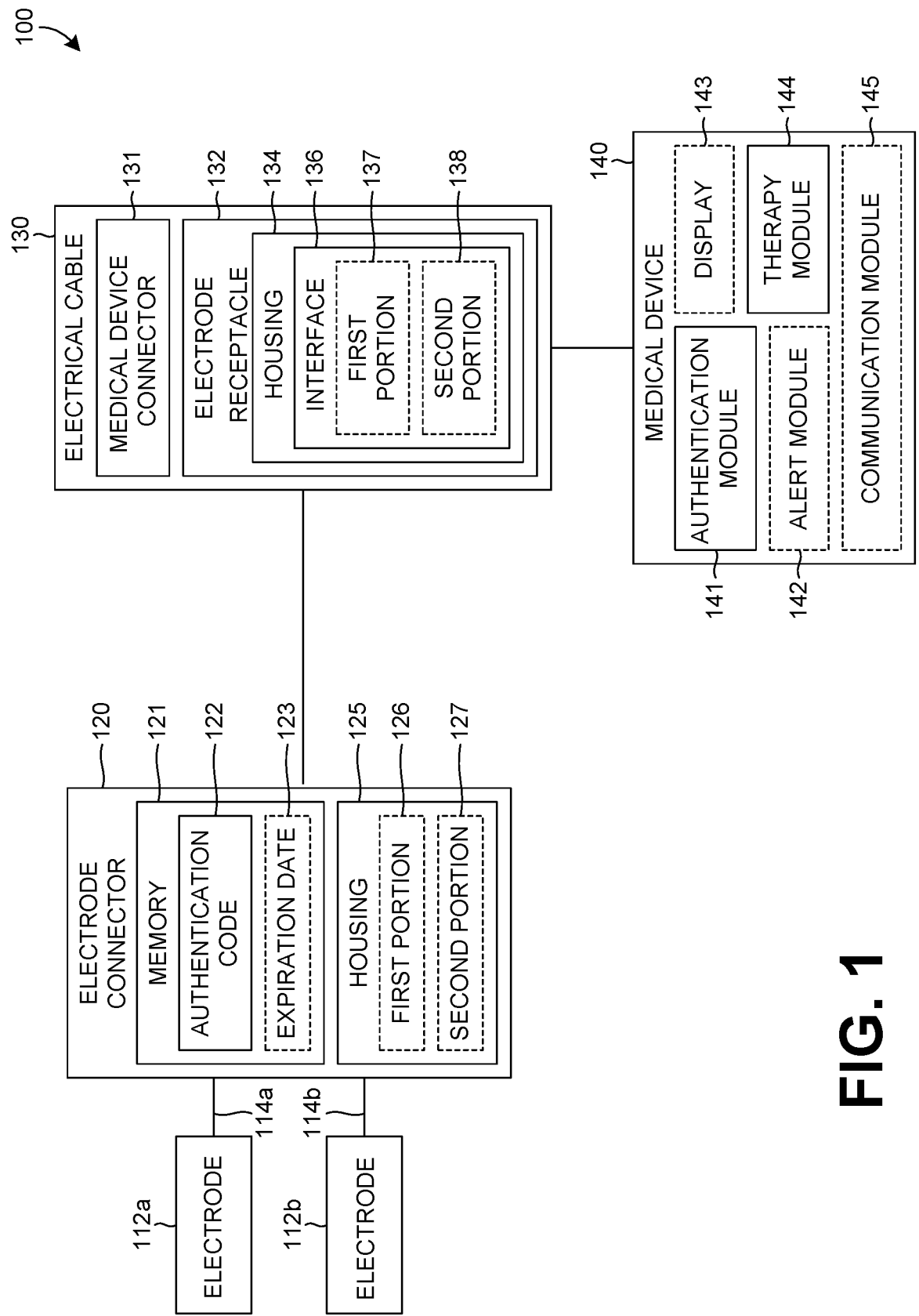
FIG. 1 illustrates an example system.

The disclosure provides electrode connector systems to ensure medical device/electrode compatibility and to determine the authenticity of coupled electrodes. Various implementations described herein relate to an electrode connector, systems that include the electrode connector, and processes involving the electrode connector. The electrode connector, the systems, and the processes described herein disclose physical and electrical features for coupling the electrode connector either to a cable that is coupled to a receptacle of a medical device, such as a defibrillator, or directly to the receptacle of the medical device. A set of electrodes, which may include one or multiple electrodes, are coupled to the electrode connector. According to some examples, the set of electrodes are configured to be used to assist with monitoring a patient, treating a patient, or both monitoring and treating a patient using the medical device. The physical features, electrical features, or combination thereof, of the electrode connector allow the electrode connector to couple to both older and newer versions of medical devices. This allows a single model of electrodes to be used with multiple versions (e.g., types, styles, models, designs, etc.) of medical devices, or vice versa, which simplifies the operations and logistics of managing or equipping multiple versions of medical devices with multiple corresponding versions of electrodes. Additionally, or alternatively, the physical features, electrical features, or combination thereof, of the electrode connector assist with verifying an authenticity of the coupled electrodes to determine if the electrodes being used with the medical device are authentic and/or not expired, which prevents unsuitable or unsafe electrodes from being used.

According to some examples, the described electrode connector includes various physical features that allow the electrode connector to couple electrodes to both an older and a newer version of a medical device, or that allow the electrode connector to couple the electrodes to both an older and a newer version of a cable that is configured to be coupled to the medical device, giving the electrode connector a "reverse compatibility" capability. The reverse compatibility capability means the electrode connector is configured to couple to both an older and a newer version of the medical device or to an older and a newer version of a cable that is configured to be coupled to the medical device. To achieve the reverse compatibility capability, the electrode connector, in some examples, includes various physical features, such as a housing that includes a first portion shaped to mate with (or be received within) a first receptacle to facilitate coupling of the electrode connector to a first version of a medical device, and a second portion shaped to mate with (or be received within) a second, different receptacle to facilitate coupling of the electrode connector to a second version of the medical device. These physical features of the electrode connector allow the electrode connector to couple to multiple versions of medical devices, thereby allowing the electrodes coupled to the electrode connector to be used with such medical devices. The reverse compatibility of the electrode connector reduces inefficiencies and expenses associated with maintaining separate versions of electrodes for use with each version of a medical device.

According to some examples, the described electrode connector includes various physical features, electrical features, or a combination thereof, that allow the coupled electrodes to be authenticated by a medical device, such as a defibrillator. An example electrical feature of the electrode connector includes a memory that stores an authentication code. According to some examples, the authentication code is stored in a clear format or an encrypted format and is provided, or made accessible, to a medical device to which the electrodes are coupled via the electrode connector. According to some examples, upon coupling of the electrode connector to a medical device, the electrode connector, or the memory of the electrode connector, is configured to permit the medical device to access (or provide the medical device with access to) the authentication code for use in authenticating the electrodes or validating the authentication code. According to some examples, the medical device uses the authentication code of the electrode connector to determine an authenticity of the coupled electrodes for use with the medical device. According to some examples, the authentication code includes, or the memory stores separately from the authentication code, a characteristic(s) of, or other information regarding, the electrodes, such as an expiration date or a type of the electrodes, for example. According to some examples, the characteristics include characteristics of the electrodes as a whole, characteristics of the individual components of the electrodes, the electrical cables coupling the electrodes to the electrode connector, or a combination of characteristics regarding the electrodes. According to some examples, the electrode connector provides an indication of the authenticity of the coupled electrodes to the medical device, and the medical device transmits the indication of the authenticity of the electrodes to an external device or system. In this manner, the use of authentic and non-authentic electrodes with the medical device is able to be tracked. According to some examples, one or more functions or features of the medical device are alterable, such as by reducing or enhancing the function(s) or feature(s), based on the determination of the authenticity of the electrodes.

FIG. 1 illustrates an example system 100 (sometimes referred to herein as a "medical device system," a "defibrillator system," an "electrode system," or a "therapy electrode system") that includes a set of electrodes 112 (sometimes referred to herein as "electrode pads") that are removably connected to a medical device 140 by an electrical cable 130 (sometimes referred to herein as a "medical device cable," or a "therapy cable"). In some examples, the set of electrodes 112 include multiple electrodes 112 (e.g., a pair of electrodes 112a, 112b, as shown in FIG. 1). In other examples, the set of electrodes 112 include a single electrode 112. In an illustrative example, the electrodes 112a and 112b are configured to be placed on a patient to sense electrical activity of a patient. According to some examples, the electrodes 112a and 112b (e.g., therapy pads) are configured to deliver electrical therapy to the patient. The electrical cable 130 is usable to provide data indicative of electrical activity sensed or detected by the electrodes 112a, 112b to the medical device 140, and the medical device 140 is configured to analyze the data and provide (e.g., display, present, emit, etc.) an output to a user that is indicative of, or that provides information regarding, the patient's electrical activity. According to some examples, the medical device 140 represents a defibrillator, but it is to be appreciated that, in other examples, the medical device 140 represents a different type of medical device, such as a patient monitor, or a similar medical device that utilizes a set of one or more electrodes 112. According to some examples, the user of the medical device 140, or the medical device 140, determines whether an electrical therapy is to be administered or delivered to the patient, and the user or the medical device 140 causes the medical device 140 to administer one or more electrotherapies based on the patient's electrical activity data or analysis thereof.

According to some examples, the electrodes 112a, 112b are connected by a respective electrical cables 114a, 114b (sometimes referred to herein as "electrode cables", "electrode wires", "wires", "electrode leads", or "leads") to an electrode connector 120. The electrical cables 114a, 114b electrically connect each of the electrodes 112a, 112b to the electrode connector 120 or portion(s) thereof. In an example, a first end of the electrical cable 114a is coupled to the electrode 112a and a second end of the electrical cable 114a is coupled to the electrode connector 120. Continuing with this example, a first end of the electrical cable 114b is coupled to the electrode 112b and a second end of the electrical cable 114b is coupled to the electrode connector 120. The electrode connector 120 is coupled to the electrical cable 130 in order to electrically couple the electrodes 112 to the medical device 140 (e.g., defibrillator). In this manner, the electrode connector 120 is an electrical connector that electrically couples a first electrode 112a and a second electrode 112b to the medical device 140 by electrical cable 130. The electrical coupling between the electrodes 112 and the medical device 140 allows for delivering electrotherapy to the patient and communicating data regarding one or more physiological parameters of the patient to or from the medical device 140. For example, the electrode connector 120 includes electrical connections for delivering electrical signals generated by the medical device 140 to the electrodes 112, as well as an electrical connection for delivering, to the medical device 140, data indicative of a physiological parameter of the patient. As used herein, the term "couple" may refer to an indirect coupling or a direct coupling between elements. The term "couple," as used herein, may also refer to a removable coupling or a permanent coupling between the elements. Elements are removably coupled if a user or another entity is able to decouple the elements. Elements are permanently coupled if a user or another entity is unable to decouple the elements without destroying or significantly damaging the elements, or without undue effort to dissemble the elements using tools or machinery. As used herein, the term "couple" can be interpreted as connect, attach, join, engage, interface, link, fasten, or bind. Unless otherwise specified herein, the term "couple" is to be interpreted as coupling elements in a mechanical sense, rather than in an electrical sense, for example. Nevertheless, it is to be appreciated that a mechanical coupling of elements may result in an electrical coupling(s) between multiple elements of the system.

According to some examples, the electrode connector 120 includes a memory 121 configured to store, or storing, an authentication code 122 and, optionally, an expiration date 123 or other information regarding the electrodes 112, such as a model number, a lot number, a production code, a type, or other characteristics of, or information regarding, the electrodes 112. According to some examples, the authentication code 122 is written to and stored securely in the memory 121, and, in some examples, the authentication code 122 is a secret code that is usable to authenticate the electrodes 112. According to some examples, the medical device 140 has one or more known and valid authentication codes and is configured to receive or retrieve the authentication code 122 of the electrode connector 120. According to some examples, the medical device 140 is configured to interpret the authentication code 122 to determine one or more characteristics of the electrodes 112. In an illustrative example, the medical device 140 is configured to compare the authentication code 122 to the one or more known authentication codes to verify the authenticity of the electrodes 112. According to some examples, the authentication code 122 is structured so that a known mathematical operation or sequence of mathematical operations using the authentication code 122 results in a value or other result that is indicative of the validity of the authentication code 122 and by association, the authentication of the electrodes 112.

According to some examples, in order to assist with the security or integrity of the authentication code 122, the authentication code 122 is encrypted or stored in an encrypted format. A key is usable to encrypt the authentication code 122 and the medical device 140 is configured to use the same or another key to decrypt the authentication code 122. In an example, the authentication code 122 is encrypted using a key and the encrypted authentication code 122 is written to or stored in the memory 121. The medical device 140 is configured to receive or retrieve the encrypted authentication code 122 and to decrypt the authentication code 122 using the same or another key. The medical device 140 is configured to compare the decrypted authentication code 122 to a listing of valid authentication codes to determine if the authentication code 122 matches one of the known, valid authentication codes. If a match is confirmed, the medical device 140 authenticates the electrodes 112, and if no match is confirmed, the medical device 140 is prevented from authenticating or cannot authenticate the electrodes 112.

According to some examples, the authentication code 122 is a series of digits or characters that is securely written to or stored within the memory 121. According to some examples, a validation process between the electrodes 112 and the medical device 140 is performed before the authentication code 122 is received or retrieved from the electrode connector 120. The secure storage of the authentication code 122 assists with preventing unauthorized parties from receiving or retrieving the authentication code 122. According to some examples, procedures or policies are enacted to allow the authentication code 122 to be securely stored in the memory 121, so that the integrity of the authentication code 122 is maintained during the process of storing the authentication code 122 within the memory 121.

According to some examples, the authentication code 122 includes various other information, or provides representations or indications of various other information, such as the expiration date 123 of the electrodes 112, a model number, a lot number, a production code, a type, or other characteristics of, or information regarding, the electrodes 112. According to some examples, the additional information is represented by values, digits or characters of the authentication code 122. According to some examples, the authentication codes 122 is structured so that various positions within the authentication code 122 are designated to denote information regarding the electrodes 112. In an example, the authentication code 122 has a length of 16 digits, with digits 1-8 being the authentication portion of the authentication code 122 and digits 9-16 being used to represent other information, such as digits 9-14 indicating an expiration date of the electrodes 112 and digits 15-16 indicating a model or type of the electrodes 112. According to some examples, during processing of the authentication code 122, the medical device 140 parses the various information contained in the authentication code 122. In an example, the medical device 140 provides an output or configures itself based on the processing of the authentication code 122, such as adjusting various settings based on the type of electrodes 112 indicated by the authentication code 122.

According to some examples, the expiration date 123 of the electrodes 112 is indicative of a date past which the electrodes 112 are no longer guaranteed or anticipated to be fully functional or to function as expected. According to some examples, the electrodes 112 include various elements or materials having an expected lifespan. According to some examples, the expiration date 123 is based on such lifespans or other factors affecting the period during which the electrodes 112 are considered safe or acceptable for use. With the use of electrodes 112 past the expiration date 123, there is a risk of reduced performance for patient diagnostics and treatment. According to some examples, in order to assist with preventing the use of expired electrodes, the expiration date 123 for the electrodes 112 is stored in the memory 121 and is received or retrieved by the connected medical device 140. According to some examples, the medical device 140 indicates the expiration date 123 or that the current date is past the expiration date 123, such as by outputting the expiration date 123 to a user to allow the user to determine if the electrodes 112 should be replaced with a newer or non-expired set of electrodes.

According to some examples, the memory 121 of the electrode connector 120 is also configured to be used to store information or data associated with (e.g., collected during) a session in which the electrodes 112 were used. According to some examples, the medical device 140 is configured to transmit information to the electrode connector 120 that is stored in the memory 121. According to some examples, the information to be stored is provided by the medical device 140 at the end of, or during, the session in which the electrodes 112 are used. According to some examples, the information provided by the medical device 140 for storage in the memory 121 includes patient physiological data collected during the session, data regarding the administration of one or more treatments during the session, a user of the medical device 140, a chronology of events during the session, or other information regarding the session. According to some examples, the stored information of the session is retrieved from the memory 121 of the electrode connector 120, such as for post event review, further treatment of the patient, or for other purposes. In an example, a treatment session of a patient begins in the field where the electrodes 112 are first applied. Treatment being administered to the patient, or portion(s) thereof, is tracked by the medical device 140 and data indicative of the tracked treatment is transmitted to the electrode connector 120 for storage in the memory 121. The patient is transported to a facility where treatment of the patient continues. When care of the patient is transferred from emergency medical services (EMS) to the facility, the electrodes 112 remain with the patient, such as affixed to the patient. A medical device of the facility is coupled to the electrode connector 120 and the session information or data stored in the memory 121 is received or retrieved to provide historical information regarding the treatment of the patient, which assists with care continuity during the further treatment and assessment of the patient. As the patient continues to receive treatment, the additional session information or data is stored in the memory 121. In this manner, a chronological history of the session is compiled and stored within the memory 121. After the session is completed, the session information or data stored in the memory 121 is received or retrieved for analysis or assessment, such as analysis or assessment that is part of a post-event review process. According to some examples, the session information or data is received or retrieved from the memory 121 and stored, such as in a database. Further, the medical device to which the electrodes 112 are connected receives or retrieves the session information from the memory 121 upon completion of the session and transmit the information to a remote device, system or location.

According to some examples, the housing 125 of the electrode connector 120 includes a mating surface(s) that interface(s) with the electrical cable 130 to couple the electrodes 112 to the medical device 140. According to some examples, in order to assist with the coupling, the housing 125 includes a first portion 126 and/or a second portion 127 that individually, or together, form the mating surface(s) that allows the electrode connector 120 to couple to the electrical cable 130 or to the medical device 140. According to some examples, the first and/or second portions 126, 127 are, or include, physical features that allow or prevent a coupling between the electrodes 112 and a medical device 140 or the electrical cable 130. According to some examples, the electrode connector 120 is configured to be coupled to one or more types of electrical cables based on the housing 125, which includes the first and/or second portions 126, 127. According to some examples, the first portion 126 of the housing 125 is shaped to fit, such as shaped to mate to (or be received within), a complementary portion of the electrical cable 130, such as a first portion 137 of the electrical cable 130, to allow the electrode connector 120 to couple to the electrical cable 130. According to some examples, the second portion 127 of the housing 125 is shaped to fit, such as shaped to mate to (or be received within), a complementary portion of the electrical cable 130, such as a second portion 138 of the electrical cable 130, to allow the electrode connector 120 to couple to the electrical cable 130. That is, the electrode connector 120 is configured to be coupled to the electrical cable 130 or the medical device 140, such as a defibrillator, having an interface that is complementary to one or both of the portions 126, 127 of the housing 125 of the electrode connector 120. This configures the electrode connector 120 having both portions 126, 127 to be coupled to two different types of receptacles, at least one of which is included in the electrical cable 130 or the medical device 140. This, in turn, allows the electrode connector 120 having both portions 126, 127 to be coupled to an older version and a new version of an electrical cable 130 or medical device 140.

In an example, a first version of electrical cable 130 has an interface 136 or receptacle 132 that allows an electrode connector 120 having the first portion 126 to be coupled to the interface 136 or receptacle 132, and a second version of electrical cable 130 has an interface 136 or receptacle 132 that allows an electrode connector 120 having the second portion 127 to be coupled to the interface 136 or receptacle 132. Electrode connectors 120 having both the first and second portions 126, 127 are configured to be coupled to both the first version and the second version of the electrical cable 130. In a case where the first version of electrical cable 130 is an older version and the second version of electrical cable 130 is a newer version, electrode connectors 120 having both the first and second portions 126, 127 have reverse compatibility, allowing the electrodes 112 to be coupled to both the newer and older versions of the electrical cable 130. In an example, the older version electrical cable 130 is used with an older model of medical device 140 (e.g., defibrillator) that lacks authentication capability, and the newer version electrical cable 130 is used with a newer model of medical device 140 (e.g., defibrillator) having the authentication capability. The reverse compatibility of the electrode connector 120 allows the electrodes 112 to be used with older and newer models of medical device 140 (e.g., defibrillator) or electrical cable 130. The reverse compatibility nature of the electrode connector 120 allows users to purchase or use electrodes 112 that are compatible with both newer and older versions of medical devices 140 (e.g., defibrillators), which eases purchasing, tracking, or stocking of the electrodes 112 for use with the various versions of medical device 140 (e.g., defibrillator) in use by the user.

In an example, the housing 125 of electrode connector 120 includes both the first and second portions 126, 127 to allow the electrode connector 120 to be coupled to both an electrical cable 130 having an interface 136 that is complementary to the first portion 126 of the electrode connector housing 125 and another electrical cable 130 having an interface 136 that is complementary to the second portion 127 of the electrode connector housing 125. According to some examples, the first and second portions 126, 127 of the housing 125 are arranged relative to each other, such as arranging the first portion 126 interior to the second portion 127, to allow the electrode connector 120 to be coupled to electrical cables 130 having an interface 136 complementary to either the first or second portions 126, 127.

According to some examples, the electrical cable 130 includes a medical device connector 131 that is configured to couple to a port or receptacle of the medical device 140, such as a defibrillator. According to some examples, the electrical cable 130 also includes an electrode receptacle 132 configured to couple to the electrode connector 120. According to some examples, the electrodes 112 are configured to couple to the medical device 140 indirectly via the electrical cable 130. In other examples, the electrodes 112 are configured to couple to the medical device 140 directly via a receptacle of the medical device 140.

According to some examples, the electrode receptacle 132 of the electrical cable 130 includes a housing 134 having an interface 136 (sometimes referred to herein as a "mating surface"). According to some examples, the interface 136 is itself a receptacle configured to receive the electrode connector 120 and the interface 136 has a first portion 137 that is compatible with, or complementary to, the first portion 126 of the electrode connector 120, or the interface 136 has a second portion 138 that is compatible with, or complementary to, the second portion 127 of the electrode connector 120. According to some examples, the interface 136 has a first portion 137 that is physically structured to allow electrode connectors 120 having the first portion 126 to be coupled to the electrical cable 130 and to prevent electrode connectors 120 that do not have the first portion 126, such as an electrode connector 120 having the second portion 127 or another portion without the first portion 126, from coupling to the electrical cable 130. According to some examples, the interface 136 has a second portion 138 that is physically structured to allow electrode connectors 120 having the second portion 127 to be coupled to the electrical cable 130 and to prevent electrode connectors 120 that do not have the second portion 127, such as an electrode connector 120 having the first portion 126 or another portion without the second portion 127, from coupling to the electrical cable 130. According to some examples, a first electrical cable 130 or first medical device 140 has an interface, such as a receptacle, with first and second portions 137, 138 that allow the first and second portions 126, 127 of the electrode connector 120 to mate with and couple to the first cable interface 136. Whereas, a second electrical cable 130 or second medical device 140 has an interface, such as a receptacle, with first and second portions 137, 138 that allow the first portion 126 of the electrode connector 120 to mate with and couple to the second electrical cable 130 but the second portion 138 of the interface of the second electrical cable 130 prevents the coupling of the second portion 127 of the electrode connector 120. In this manner, the interface 136 selectively allows electrode connectors 120 to be coupled to the electrical cable 130 by physically preventing electrode connectors 120 having a certain portion, such as 126 or 127, from being connected to the electrical cable 130. By preventing electrode connectors 120 having certain portions, such as 126, 127, from being connected, the interface 136 of the electrical cable 130 helps ensure that a suitable model of electrodes 112 is used with the electrical cable 130.

According to some examples, electrode connectors 120 having both the first and second portions 126, 127 are configured to couple to electrical cables 130 that include an interface 136 having either the first portion 137 or the second portion 138. That is, according to some examples, electrode connectors 120 having both the first and second portions 126, 127 are used with multiple versions of an electrical cable 130. In an example, an older version of the electrical cable 130 has an interface 136 having the first portion 137 and a newer version of the electrical cable 130 has an interface 136 having the second portion 138. According to some examples, an electrode connector 120 having the first and second portions 126, 127 has reverse compatibility that allows the electrode connector 120 to be coupled to either of the versions of the electrical cable 130. According to some examples, the medical device 140 itself has an interface similar to, or the same as, the interface 136 of the electrical cable 130 described herein.

According to some examples, the medical device 140 (e.g., defibrillator) is configured to receive or sense one or more patient physiological parameters or treatment administrations via the electrodes 112 and administers an electrotherapy via the electrodes 112 connected by the electrical cable 130. According to some examples, the medical device 140 processes and analyzes various received or provided information or inputs to determine whether to administer an electrotherapy to a patient or not. According to some examples, the medical device 140 includes an authentication module 141, an alert module 142, a display 143, a therapy module 144, and a communication module 145 to assist or perform one or more functions or features of the medical device 140.

According to some examples, the authentication module 141 is configured to analyze and process the authentication code 122 retrieved or received from the electrode connector 120 to determine whether the electrodes 112 are authentic or not, such as by confirming the authentication code 122 to the medical device 140 as authentic or valid. According to some examples, analyzing and processing the authentication code 122 includes comparing the authentication code 122 to a stored list of valid authentication codes and performing various operations using the authentication code 122, such as decrypting or parsing the authentication code 122. In an example, the authentication module 141 securely maintains a list of authentication codes and is configured to compare the received authentication code 122 to the list. According to some examples, the list of authentication codes includes previously and currently valid authentication codes and is updatable, such as by communication(s) received by the communication module 145. According to some examples, updates to the list of authentication codes are provided in a secure manner by a manufacturer or other trusted party. If the received authentication code 122 is listed as a currently valid authentication code, the authentication module 141 authenticates the electrodes 112. If the received authentication code 122 is not listed or is not currently listed as a valid authentication code, the authentication module 141 does not authenticate the electrodes 112.

According to some examples, the authentication codes of the list accessible to the authentication module 141 include corresponding expiration data indicating a time period during which one or more authentication codes of the list are consider authentic. In an example, authentication codes of the list are invalidated after a set period of time based on an expiration date of the electrodes 112. In this manner, electrodes 112 associated with an authentication code 122 that was previously valid are considered authentic but expired and are not advisable, or suitable, for use. Based on this, the authentication module 141 causes the medical device 140 to notify or alert a user, such as by the alert module 142 or display 143, that the electrodes 112 are expired or are authentic but not valid due to the expiration date. In an example, the medical device 140 requests that the user provide an input acknowledging the alert to continue operating the medical device 140 with the non-authenticated electrodes 112 connected thereto. The user's positive acknowledgement to continue a session with non-authenticated electrodes 112 is noted in the history or chronology of the session, which is stored in the memory 121 of the electrode connector 120. According to some examples, an alert regarding the authenticity of the electrodes 112 is not output and the use of non-authenticated electrodes 112 is recorded in the session history which is stored by the medical device 140 and in the memory 121 of the electrode connector 120.

In another example, the validity of the authentication code 122 is determined using a predetermined routine of operations that are performed using the received authentication code 122, such as one or more mathematical operations. Based on the results of routine, the validity of the authentication code 122 is determined by the authentication module 141. According to some examples, the routine includes an operation(s) that determine the validity of the authentication code 122, such as a time-based component of the routine that indicates if the electrodes 112 are expired or not.

According to some examples, the operation of the medical device 140 is alterable or modifiable based on a determination that non-authenticated electrodes 112 are being used or are connected to the medical device 140. Due to the inherent uncertainty regarding the characteristics, such as the performance or tolerances, of the non-authenticated electrodes 112, there is a risk of reducing the performance of the medical device 140. According to some examples, reducing the performance includes altering a confidence of an analysis or processing of physiological parameter data, altering thresholds used for one or more determinations based on the physiological parameter data collected, or altering other operations or parameters of the medical device 140. According to some examples, manual control of the medical device 140 and its operations is provided to a user during use of the medical device 140 with non-authenticated electrodes 112. However, according to some examples, one or more automated assessments or analyses performed by the medical device 140 are associated with an increased margin of error, or reduced tolerances, due to the uncertainty caused by using the medical device 140 with the non-authenticated electrodes 112. As such, according to some examples, the medical device 140 operates relatively the same with authenticated and non-authenticated electrodes; however, the use of non-authenticated electrodes reduces the efficiency or effectiveness of the medical device 140, which can be purposeful or a result of the use of non-authenticated electrodes.

According to some examples, the medical device 140 is purposefully operated with the reduced efficiency or effectiveness due to the uncertainty in various analyses and assessments caused by the uncertainty regarding the properties, or characteristics of the non-authenticated electrodes 112. According to some examples, the uncertainty causes the analyses and assessments of the medical device 140 to be based on more definitive, confident, or positive indications of the accuracy of the analyses and assessments, which takes additional time or detects greater changes in various physiological parameters of the patient before providing the analyses or assessments. According to some examples, the increased time, or tolerances, of the analyses or assessments using non-authenticated electrodes 112 reduces the efficiency of performing such analyses or assessments compared to when authenticated electrodes 112 are used with the medical device 140. According to some examples, this reduced efficiency or effectiveness is implemented as a safety procedure to protect the patient from error in analyses, assessments, or therapy administrations due to the inherent uncertainty caused by the use of non-authenticated electrodes 112.

In an illustrative example, a non-authenticated electrode 112 is detected by measuring or sensing a value(s) associated with one or more characteristics of the electrode 112, such as an electrical characteristic(s) of an electrode circuit, and comparing the measured or sensed value(s) against a value or range of values that are assumed in one or more of the assessments or analyses performed by the medical device 140. According to some examples, the assessments or analyses performed by the medical device 140 include patient monitoring and diagnostics of various conditions, including conditions that are treatable by delivering a shock to a patient in an attempt to correct a cardiac arrhythmia or to administer or forego administration of some other active treatment that helps promote a positive patient outcome. According to some examples, the patient monitoring and diagnostics are performed based on sensed, measured, or input patient physiological data, which includes data that is sensed or measured by various sensors coupled to the patient that sense and transmit data to the medical device 140 for use by the diagnostic and treatment algorithm or data that is input by a rescuer about the patient or is input from a patient health record.

According to some examples, finely-tuned algorithms are performed to automatically output recommendations or instructions or provide output to a user to take action in response to certain patient conditions that are diagnosed or otherwise indicated by the diagnostic and treatment algorithm. Those finely tuned algorithms assume specific tolerances in various electrical properties of the electrode components, such as inductance, resistance, and capacitance value(s) or any sub-combination of these values or all three values. The electrical properties to which the algorithms are tuned may vary in different diagnostic and treatment algorithms and any suitable additional electrical property(ies) may be included and any of the disclosed electrical properties may or may not be included in alternative examples of the diagnostic and treatment algorithm.

In an illustrative example, when an electrode 112 is coupled to both a patient and a medical device 140, the inductance of the electrode 112 is automatically measured by the medical device 140. That inductance value is compared to a range of inductance values tolerated by the diagnostic and treatment algorithm that automatically diagnoses and treats the patient. According to some examples, the comparison of the sensed or measured inductance value to the range of inductance value(s) is performed by the authentication module 141 or another software module. According to some examples, a look-up table of inductance values tolerated by the diagnostic and treatment algorithm is stored in memory of the medical device 140 or other memory accessible by the medical device 140. If the inductance value of the coupled electrode 112 is within the range of inductance values tolerated by the medical device 140, then the diagnostic and treatment algorithm continues to diagnose and treat the patient according to its pre-set assumptions with full confidence applied to the resulting diagnoses and treatments. However, if the inductance value of the coupled electrode 112 falls outside of the tolerated range of inductance values for the diagnostic and treatment algorithm, then error in one or both of diagnosis and treatment of the patient can occur. Because defibrillators (a type of medical device 140) are life-saving devices, accuracy of their diagnostic and treatment algorithms is a factor in both properly diagnosing and then treating the patient, or there is a risk that the patient may die. According to some examples, error is potentially introduced when incompatible electrodes 112 or electrodes 112 that are less-than-ideally-compatible with the diagnostic and treatment algorithm are coupled to the medical device 140 (e.g., defibrillator) because non-authenticated electrodes 112 have electrical properties that fall outside of the assumptions made by the diagnostic and treatment algorithm to one or both of diagnose and treat the patient. Such electrical properties that are not within the tolerated range of values for authenticated electrodes introduce the potential for error in the diagnoses and treatment of patients, which reduces or even eliminates the likelihood of a positive patient outcome. The authentication module 141 disclosed herein serves as a failsafe to allow the diagnostics upon which treatment is administered to be more accurate.

Some electrodes 112 are not able to be authenticated to the medical device 140, which causes the diagnostic and treatment algorithm to operate at less than maximum capacity. According to some examples, those electrodes 112 that fail the authentication process have electrical properties that are measured or sensed to be outside of the range of values tolerated by the diagnostic and treatment algorithm or their values are not confirmed to be within the tolerated values. When this occurs, the electrode 112 is designated as non-authenticated. In some examples, the authentication module 141 or another module automatically or manually generates an instruction to the diagnostic and treatment algorithm to reduce its diagnostic and treatment functionality when an unauthenticated electrode 112 is detected. According to some examples, the authentication module 141 or another module generates an instruction to alter a function of the medical device 140 based on whether the electrode 112 is identified to be authenticated or non-authenticated. According to some examples, the authentication module 141 or other module automatically disables certain diagnostic functions of the diagnostic and treatment algorithm or function(s) of the medical device 140 that rely on the electrical properties in the electrodes 112 falling within the tolerated range, which includes certain advanced diagnostic functionality in some examples.

In other examples, the diagnostic and treatment algorithm outputs an instruction to a rescuer to confirm a treatment instead of instructing the medical device 140 (e.g., defibrillator) to automatically administer the treatment, such as delivery of a defibrillation shock. In still other examples, a reduced confidence score is applied to the results of the diagnostic and treatment algorithm for the patient, which alters the availability or certain functionality or changes the type of functionality applied by the diagnostic and treatment algorithm to the resulting data. Any functionality or combination of functionalities of the medical device 140 for administering patient monitoring or treatment may be reduced, disabled, or applied differently based on the electrodes 112 failing to be authenticated to the medical device 140.

According to some examples, the authentication module 141 parses the received authentication code 122. In an example, the authentication code 122 includes additional information contained therein, such as an expiration date 123, a type of the electrodes 112 or other information regarding the electrodes 112. According to some examples, the authentication code 122 is structured so that known positions, or digits, within the authentication code 122 correspond to one or more other pieces of information. According to some examples, the authentication module 141 parses the authentication code 122 based on a predetermined structure of the authentication code 122 and processes the various information contained therein, including information indicating the authenticity of the authentication code 122. In an example, the authentication code 122 includes expiration information that is parsed, or processed, by the authentication module 141. The authentication module 141 determines an expiration date of the electrodes 112 from, or based on, the authentication code 122 and compares the expiration date to a current date to determine if the electrodes 112 are expired. If the authentication module 141 determines the electrodes 112 are expired, the authentication module 141 causes an alert to be output to a user of the medical device 140, such as by the alert module 142 or via the display 143. According to some examples, the user provides an acknowledgement of the expired status of the connected electrodes 112 before being allowed to proceed. According to some examples, the expired status of the electrodes 112 is noted in the session history, which is stored in the memory 121 of the electrode connector 120 and which is stored by the medical device 140.

According to some examples, the authentication code 122 includes a type of the electrodes 112, such as whether the electrodes 112 are for adults or for children, which is parsed or processed by the authentication module 141. In an example, the authentication module 141 causes, or provides an output causing, the medical device 140, or setting(s) thereof, to be configured for use based on the type of the electrodes 112. That is, based on the determined type of the electrodes 112 connected to the medical device 140 (e.g., defibrillator), the medical device 140, according to some examples, is automatically configured. In an example, magnitude of available electrotherapy outputs is reduced or constrained based on a determination that the electrodes 112 are a pediatric type. In another example, the treatment instructions and guidance, or the physiological parameter monitoring or processing, by the medical device 140, is modified based on the type of patient being treated, as indicated by the type of the electrodes 112 connected to the medical device 140.

According to some examples, other information regarding the electrodes 112, such as the expiration date 123, type, or other information, is stored in the memory 121 of the electrode connector 120. The authentication module 141, or another module, element, or system of the medical device 140 is configured to receive or retrieve this other information from the memory 121 of the electrode connector 120. Based on the other information, the operation of the medical device 140 is modified or altered, such as altering one or more settings or parameters to configure the medical device 140 for a pediatric or an adult patient. The automatic configuration of the medical device 140, based on the information regarding the electrodes 112 connected thereto, assists with increasing the efficiency and accuracy of using the medical device 140 by reducing the amount of manual setup required of a user and by preventing incorrect applications of an electrotherapy.

According to some examples, data or information regarding the electrodes 112, and their use, is collected by the medical device 140 and stored, such as in the memory 121 of the electrode connector 120 or in memory of the medical device 140, and the data or information is transmitted to another device or system, such as by the communication module 145. According to some examples, the data or information regarding the electrodes 112 and their use is analyzed to assess performance of the electrodes 112, such as for performance deficiencies or errors, and to collect data or generate statistics or metrics regarding the electrodes 112.

For example, the use of non-authenticated electrodes 112 with the medical device 140 is tracked or monitored. According to some examples, the non-authenticated electrodes 112 are non-OEM (original equipment manufacturer) or third-party accessories that are not certified or validated for use with the medical device 140, such as by a regulatory agency or a manufacturer of the medical device 140. Such electrodes 112 are not guaranteed to have or meet the required specifications regarding the manufacture and performance of the authenticated electrodes 112. Use of the non-authenticated electrodes causes reduced performance of the medical device 140, such as a reduced precision in determining or analyzing the received patient physiological parameter data or reduced efficacy of discharged therapies. According to some examples, the use of non-authenticated electrodes 112 are tracked due the potential adverse impact(s) on the performance and use of the medical device 140. A manufacturer tracks and monitors the use of the non-authenticated electrodes for various reasons, such as to assess the efficacy of using such electrodes 112 or to investigate the reasons why users are using such electrodes 112.

According to some examples, the alert module 142 generates an alert based on one or more analyses, processes, or statuses of the medical device 140, or a component or system thereof, such as the authentication of the electrodes 112. According to some examples, the generated alert is output by the medical device 140, such as via the display 143, an audible output via a speaker(s), or other output of the medical device 140. The output of the generated alert directs a user's attention to important information regarding the medical device 140 or its functions or features. Additionally, the generated alert is associated with a class that affects the manner in which the alert is output. In an example, alerts are classified by their importance, such as a first class for a critical or informative alert. Alerts having a higher importance (e.g., in the first class) are output in a manner that quickly directs the user's attention to the alert, such as by an audible or displayed output(s) having a high intensity or visual impact (e.g., a loud sound, a bright color, large font, flashing light, etc.). Alerts having a lower importance are classified as such (e.g., in a second class) and are output in a reduced-intensity manner, such as by a reduced volume of an audible output or displaying the alert in a reduced or standard manner (e.g., neutral tone color, moderate size font, etc.) on the display 143. According to some examples, the generated alert includes a request for a user input or acknowledgement, such as providing a prompt for user selection, to verify or acknowledge that the user has received, read, or noticed the alert. According to some examples, the generated alert causes a transmission or communication by the communication module 145 regarding the alert. In an illustrative example, the alert is transmitted to an external device or system and the alert optionally includes accompanying information regarding the alert. In another example, the generated alert causes an entry to be generated in the session history based on the alert. According to some examples, generating the entry in the session history includes logging or recording other information, such as the cause of the alert, patient physiological data, or other information available at the time of the alert.

In an example, alert module 142 is configured to generate an alert based on the result of the authentication of the electrodes 112 by the authentication module 141. In this manner, the user is alerted as to whether the electrodes 112 are authenticated based on the authentication code 122 received from the electrode connector 120. If the electrodes 112 are determined to be authenticated, such as by the authentication module 141, the alert module 142 generates an alert that is an audible, tactile (e.g., vibratory), or displayed indication that indicates the authenticated status of the electrodes 112. According to some examples, such an alert is classified in a class associated with a reduced or standard notification importance since it is the expected outcome of the authentication process. If the electrodes 112 are determined to not be authenticated, the alert module 142 generates an alert that the electrodes 112 are not authenticated. Since such a determination is potentially impactful on patient monitoring or treatment, such an alert is classified in a class associated with a high level of importance. The high importance of the alert causes the alert to be output by the medical device 140 in a manner that is likely to grab the attention of a user (e.g., loud sound, bright color, large size font, strong vibration, flashing light, etc.). According to some examples, the non-authenticated determination of the electrodes 112 causes the alert module 142 to output an alert that is communicated to an external device or system by the communication module 145. As previously discussed, the use of non-authenticated electrodes 112 with the medical device 140 is tracked, and optionally recorded, for statistical, analytical, performance, marketing or other considerations.

According to some examples, the display 143 of the medical device 140 is a screen or other visual output that displays information or data for a user to view. According to some examples, the display 143 is an input device, such as a touchscreen, to allow the user to interact with the displayed content. According to some examples, the display 143 displays patient physiological parameter data or analyses, such as patient electrical activity monitored using the electrodes 112, or other information regarding the medical device 140, function or features of the medical device 140, or other information. According to some examples, alerts or notifications, such as those generated by the alert module 142, are output to a user by the display 143. In an example, the authentication module 141 causes or generates an output to cause the authentication status of the electrodes 112 to be shown on the display 143. This provides a visual indication to the user whether the electrodes 112 are authenticated or not. According to some examples, the display of such an indication varies based on the authentication determination. In an illustrative example, an authenticated status of the electrodes 112 is displayed on a green background, as a text message or other inconspicuous display of the status due to the low importance, or priority, of displaying the authenticated status of the electrodes 112. In another example, the electrodes 112 are not authenticated, and the displayed status of the electrodes 112 is displayed more prominently or displayed in a more noticeable or conspicuous manner, such as on a red or flashing background, as text in a larger size or more noticeable (e.g., brighter, vibrant, etc.) color or font, or in another noticeable or conspicuous manner to communicate the non-authenticated status of the connected electrodes 112.

According to some example, the therapy module 144 of the medical device 140, such as a defibrillator, is configured to output one or more treatment therapies, such as defibrillation shocks, to a patient via the electrodes 112. According to some example, the therapy module 144 includes an energy storage system to store electrical energy for the administration of one or more defibrillations or other electrical treatments. According to some example, the therapy module 144 is configured to process patient physiological parameter data, such as that collected using the electrodes 112, and to determine a therapy based on the processed data. As discussed previously, the uncertainty regarding properties or characteristics of non-authenticated electrodes 112 causes the analysis to operate, or be performed, using an increased margin of error to maintain a safe treatment of the patient. The increased margin of error reduces the efficiency of the analysis performed by the therapy module 144 when using non-authenticated electrodes 112. Alternatively, the functions or features of the medical device 140, including analyses by the therapy module 144, remains the same regardless of the use of authenticated electrodes 112 or non-authenticated electrodes 112. However, the use of non-authenticated electrodes 112 inherently reduces the efficiency of the medical device 140, or one or more functions or features thereof, due to the non-authenticated electrodes 112 having different properties or characteristics than those of authenticated electrodes 112.

According to some examples, the communication module 145 provides bidirectional or unidirectional communication capabilities between the medical device 140 and an external device or system. The communication module 145 includes or operates using one or more communication protocols, such as WiFi, Bluetooth®, cellular network, radio network or other communication protocols, networks and systems, to communicate with an external device or system. Data or information is transmitted from the medical device 140 by the communication module 145, such data or information having been collected during a treatment session, which includes an authentication status of the electrodes 112. According to some examples, such information is transmitted to an external server or system, where it is stored, processed or analyzed. Various policies or procedures are included in, or accessible to, the communication module 145 to assist with routing communications with the medical device 140. The policies or procedures assist with maintaining the integrity of the medical device 140, its functions or features, and the data gathered by the medical device 140. Considerations of privacy or security of patient data are included in the communication policies or procedures. In an example, the communication module 145 is prevented from transmitting patient data containing personally identifiable information (PII) to a location or system other than one associated with treating the patient, such as a hospital, clinic or physician. In this manner, data regarding treatment sessions is collected by a party, such as a manufacturer, to assess the performance of the medical device 140, or other elements of the treatment session, without violating policies or laws regarding the privacy and security of patient data. In another example, the session data is transmitted to a hospital, or treatment facility, to which a patient is being transported. In this manner, the facility has data or information regarding the treatment of the patient prior to the patient's arrival, which allows the facility to prepare to receive the patient, and make decisions regarding care of the patient at the facility. Alternatively, or additionally, the provided session data is used for other uses of the treatment session data by the facility or personnel associated therewith.

In the system 100 of FIG. 1, the medical device 140, according to some examples, is an automated external defibrillator (AED), a monitor-defibrillator, or other defibrillation device connectable to electrodes 112. Additionally, the electrode connector 120 is connectable directly to a port or receptacle of the medical device 140 (e.g., defibrillator), without an intervening electrical cable 130. In an example, an AED is initially used to treat or monitor the patient by placing the electrodes 112 on the patient and coupling the electrode connector 120 to a port of the AED. Emergency medical service (EMS) personnel arriving on the scene have a defibrillation device with enhanced or additional patient monitoring and treatment functions or features. The EMS defibrillation device has an electrical cable 130 connectable thereto, so the EMS personnel is able to decouple the electrode connector 120 from the AED and couple the electrode connector 120 to the EMS defibrillation device using the electrical cable 130. Patient treatment and monitoring therefore continues without having to replace or change the electrodes 112 that are attached to the patient. Additionally, data of the treatment and monitoring by the AED is transferred to the EMS defibrillation device from the memory 121 of the electrode connector 120. The patient is then transported to a facility, such as a hospital for further treatment and monitoring. At the hospital, the electrode connector 120 is disconnected from the EMS defibrillation device, for example, and connected to a hospital defibrillation device, again without requiring the electrodes 112 to be removed from the patient. Additionally, the treatment session data collected during use of the AED and the EMS defibrillation device is stored in the memory 121 of the electrode connector 120 and is accessible to the hospital defibrillation device, or another medical device. In this manner, a history of the patient treatment and monitoring is maintained while the patient is moved between various locations or responsibilities. This historical record assists with the ongoing patient treatment and monitoring, such as providing additional information on which decisions regarding patient treatment and monitoring are based.

Figure 2A:
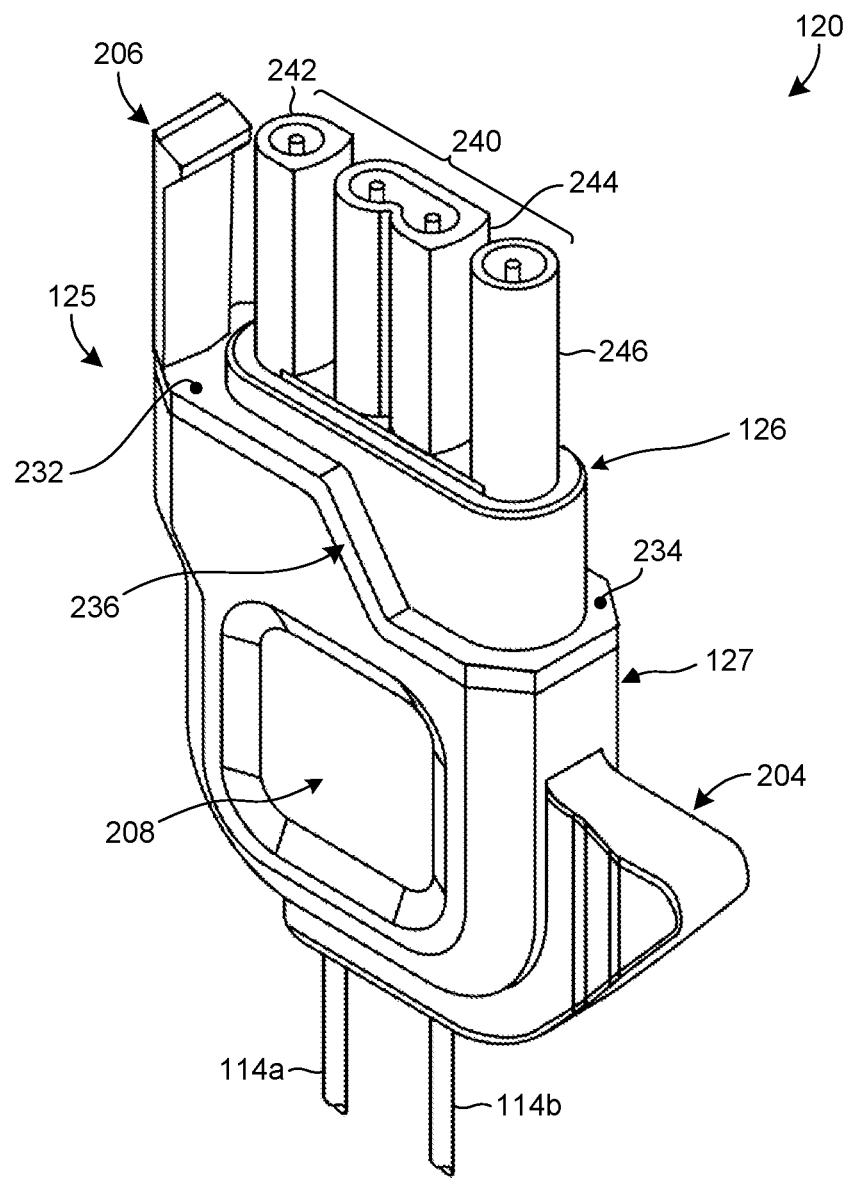
FIG. 2A illustrates a perspective view of an example electrode connector.
Figure 2B:
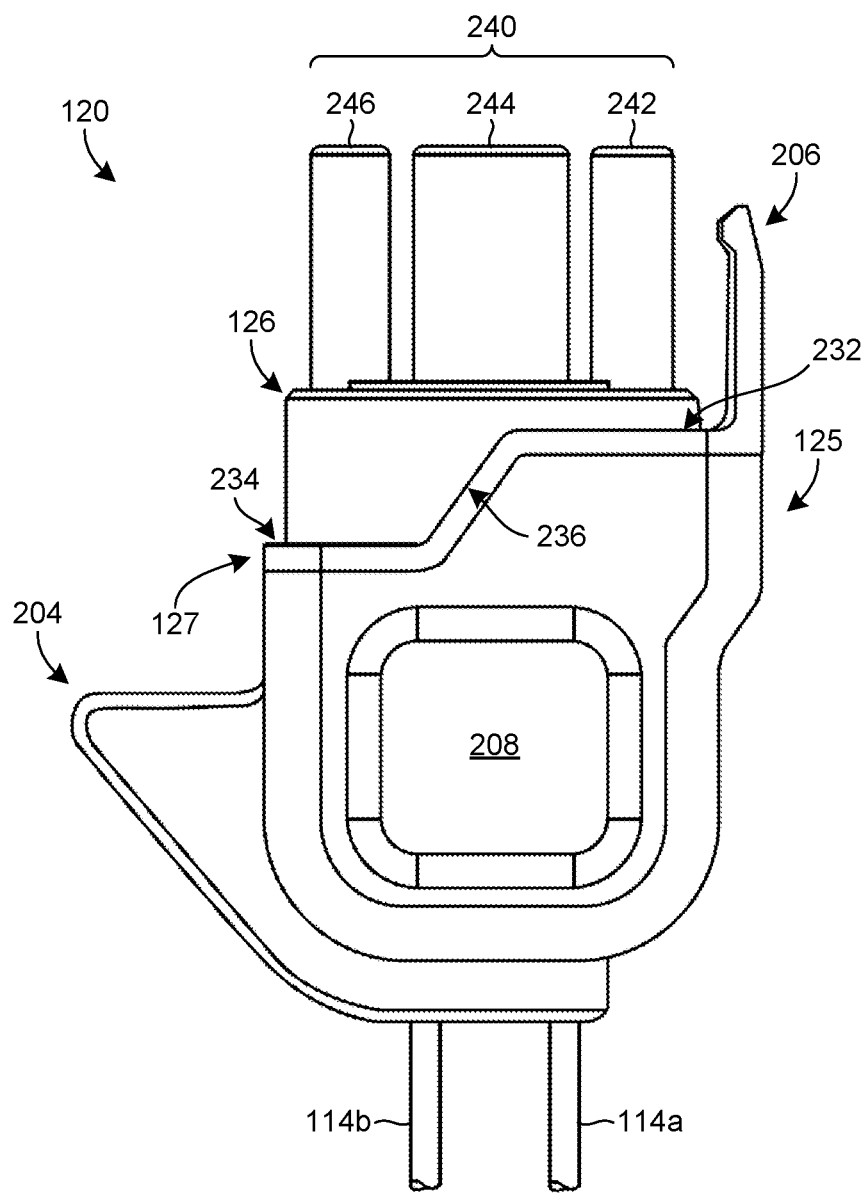
FIG. 2B illustrates a side view of the example electrode connector depicted in FIG. 2A.

FIG. 2A illustrates a perspective view of an example electrode connector 120, and FIG. 2B illustrates a side view of the example electrode connector 120 of FIG. 2A. The electrode connector 120 includes a housing 125, electrical cables 114a, 114b coupled to a proximal end of the electrode connector 120, a first portion 126, a second portion 127, and a columnar portion 240, the columnar portion 240 located at a distal end of the electrode connector 120. The electrode connector 120 is coupled to the electrodes 112 (e.g., two therapy pads 112a, 112b) by the electrical cables 114a, 114b, and the electrode connector 120 is configured to be coupled to a port, receptacle, or interface, of an electrical cable 130 or a medical device 140 (e.g., defibrillator). In some examples, various features of the electrode connector 120 prevent the electrode connector 120 from being coupled to particular ports, receptacles or interfaces of cables 130 and medical devices 140, while other features of the electrode connector 120 permit the electrode connector 120 to be coupled to other ports, receptacles or interfaces of cables 130 and medical devices 140. In other examples, the features (e.g., the first and second portions 126, 127) permit the electrode connector 120 to be coupled to different receptacles or interfaces of different versions of cables 130 and medical devices 140, as described herein.

In the example of FIGS. 2A and 2B, the housing 125 of the electrode connector 120 includes a protrusion 204, a tab 206, and a recess 208, which are each separate and interconnected or integrally formed with the housing 125. The features of the housing 125 assist a user with coupling the electrode connector 120 to, and decoupling the electrode connector 200 from, a cable 130 or medical device 140, such as assisting the user with gripping or handling the electrode connector 120, assisting the user with exerting the needed force to couple or decouple the electrode connector 120, or provide a feature with which the user intuitively interacts to manipulate the electrode connector 120. According to some examples, a level of force is required to couple and decouple the electrode connector 120 to and from the cable 130 or medical device 140, and the features of the housing 125 assists a user with exerting such force on the electrode connector 120. Additionally, this level of force assists with preventing the electrode connector 120 from being inadvertently or unintentionally disconnected from a cable 130 or medical device 140.

The housing 125, or portions thereof, may be made of any suitable material, combination of materials, or composite materials. According to some examples, the housing 125 of the electrode connector 120 is made of a semi-rigid material or a rigid material, such as a polymer material including a thermoplastic polymer, such as acrylonitrile butadiene styrene (ABS) plastic, or a similar material. According to some examples, the housing 125, or portions thereof, are manufactured using an injection molding technique, or an extrusion technique, the processes for which should be apparent to a person having ordinary skill in the art. By using an injection molding method to manufacture the housing 125, or portions thereof, minimal material is used for the manufacture of the housing 125, thereby preventing excess waste of material. Other manufacturing techniques that may be used to manufacture the housing 125 include machining a material into the shape of the housing 125. According to some examples, another subtractive manufacturing technique are used besides machining. According to some examples, an additive manufacturing technique, such as 3D printing, is used to manufacture the housing 125, or portions thereof.

According to some examples, the protrusion 204 is configured to be engaged by a finger of a user to exert a pulling force on the electrode connector 120 to uncouple, or disconnect, the electrode connector 120 from a cable 130 or medical device 140 receptacle. Additionally, the protruding nature of the protrusion 204 reduces a likelihood that a user's finger will slip from the protrusion 204 when the user is exerting the pulling force. Similarly, the large nature of the protrusion 204 allows for easily engaging the protrusion 204 by users who are wearing gloves on their hands since gloves inhibit or make more difficult a user's movements or engagement with objects. In an example, the protrusion 204 includes surface texturing or an otherwise high-friction surface to assist gripping the protrusion 204 and reducing the likelihood of a user's finger slipping when the user is engaging the protrusion 204 with a finger.

In the example of FIGS. 2A and 2B, the protrusion 204 includes a planar surface that is substantially perpendicular to a side surface of the housing 125 or to a longitudinal axis running from a proximal end to a distal end of the electrode connector 120. This planar surface is sized to accommodate an average-sized finger of a human. According to some examples, the protrusion 204 extends from the side surface of the housing 125 at least about one centimeter. That is, a most distal point of the protrusion 204 is at least about a one centimeter from the side surface of the housing 125. The planar surface of the protrusion 204 is shown as being positioned at about a center of the housing 125, between a distal end of the housing 125 and a proximal end of the housing 125. The protrusion 204 shown in FIGS. 2A and 2B further includes an inclined surface that begins near a center of the housing 125 and slopes at an angle toward a proximal end of the housing 125 where the electrical cables 114a, 114b are coupled to the electrode connector 120. In FIGS. 2A and 2B, the protrusion 204 is positioned on a side of the housing 125 opposite the side where the tab 206 is positioned. The electrode connector 120 shown in FIGS. 2A and 2B includes two opposing sides with larger surfaces and two opposing sides with smaller surfaces, which are smaller than the larger surfaces. The protrusion 204 shown in FIGS. 2A and 2B extends from one of the sides of the electrode connector 120 having the smaller surface.

The tab 206 prevents or reduces the unintended disconnection of the electrode connector 120 from a cable 130 or medical device 140. The cable 130 or medical device 140 to which the electrode connector 120 is connectable includes a recess, or other feature, for receiving the tab 206, or portion thereof. As the electrode connector 120 and the cable 130 or medical device 140 are connected, the tab 206 slides along a portion of the cable 130 or medical device 140 until the tab 206 couples to the recess or feature of the cable 130 or medical device 140. A portion of the tab 206, such as a protrusion, is configured to couple to the recess, or feature, of the cable 130 or medical device 140, and the coupling of the tab 206 is an additional connection integrity feature that has to be overcome to decouple the electrode connector 120 from the cable 130 or medical device 140. In some examples, in order to decouple the electrode connector 120 from the cable 130 or medical device 140, the tab 206 or the electrode connector 120 is manipulated to decouple the tab 206 from the recess or feature of the cable 130 or medical device 140 to allow the electrode connector 120 to be decoupled.

The tab 206 shown in FIGS. 2A and 2B extends from a distal end of the electrode connector 120 and is positioned to one side of the housing 125. In this manner, the tab 206 is positioned on a side of the housing 125 that is opposite the side where the protrusion 204 is positioned. The tab 206 includes a protrusion itself, which extends inward toward a middle of the electrode connector 120. According to some examples, the tab 206 is flexible or bendable, but resilient such that the tab 206 flexes outward and away from a middle of the electrode connector 120 while coupling the electrode connector 120 to a cable 130 or medical device 140, and the resilient nature of the tab 206 allows the tab 206 to spring back toward a middle of the electrode connector 120 when the protrusion of the tab 206 slides into a corresponding recess. Once coupled to (e.g., engaged within) the recess, the protrusion extending from the tab 206 helps to retain the electrode connector 120 in a coupled state or condition by preventing movement in a direction parallel to the longitudinal axis running from the proximal end to the distal end of the electrode connector 120.

The recess 208 shown in FIGS. 2A and 2B is formed on a side of the electrode connector housing 125 having a larger surface than the side from where the protrusion 204 extends. This recess 208 provides a location for a user to grasp and engage with the electrode connector 120. A user pinches or grasps the electrode connector 120 with a finger positioned in the recess 208. The user guides and aligns the electrode connector 120 with a receptacle of the cable 130 or medical device 140 and exerts a force on the electrode connector 120 to couple the electrode connector 120 to the cable 130 or medical device 140. The recess 208 allows the user to more easily grip the electrode connector 120 and to exert the necessary force on the electrode connector 120 to couple the electrode connector 120 to, or decouple the electrode connector 120 from, the cable 130 or medical device 140.

The recess 208 shown in FIGS. 2A and 2B is substantially square shaped, but any suitable shape can be defined in a side surface of the housing 125 for creating the recess 208 (e.g., a circular shape, triangular shape, etc.). The recess 208 spans an area on the side surface of the housing 125 that is large enough to accommodate an average-size finger. According to some examples, the area of the recess 208 is about four square centimeters. The recess 208 shown in FIG. 2A is a first recess defined on a first side of the electrode connector 120, while the recess 208 shown in FIG. 2B is a second recess defined on a second side of the electrode connector 120, the second side opposite the first side. Thus, the housing 125 includes two recesses 208 defined in opposing side surfaces of the housing 125.

In the example shown, the housing 125 of the electrode connector 120 includes a first portion 126 and a second portion 127. Each of the portions 126, 127 is shaped and sized to couple to a complementary receptacle, such as a receptacle sized and shaped to receive either or both of the portions 126, 127. In an example, the first portion 126 is sized and shaped to couple to a receptacle of an older version of the medical device 140 (e.g., defibrillator) or a cable 130 for use with an older version of the medical device 140. In the example, the second portion 127 is sized and shaped to couple to a receptacle of a newer version of the medical device 140 or a cable 130 for use with a newer version of the medical device 140. In this manner, the electrode connector 120 is reverse compatible and is able to couple to multiple versions of medical devices 140 or cables 130. Such reverse compatibility provides one or more benefits to users, such as those having one or more versions of a medical device 140 or cable 130. The reverse compatibility allows a user to stock or order a single type of electrodes 112 (or electrode package), having the reverse compatible electrode connector 120, for use with both older and newer versions of a medical device 140, which reduces the costs and logistics to acquire or maintain supplies for both the older and newer versions of the medical device 140. Additionally, efficiency is increased, or errors reduced, since users do not need to consider if they have the correct electrodes 112 (or electrode package) since the electrode connector 120 is compatible with both the newer and older versions of the medical device 140.

The first portion 126 has a cross-section (taken transversely through the electrode connector 120 in a transverse plane between the proximal end and the distal end of the electrode connector 120), the cross-section of the first portion 126 being oblong-shaped (e.g., ovoid-shaped) with rounded ends. The first portion 126 includes a vertically-oriented mating surface that is aligned with a longitudinal axis running from a proximal end to a distal end of the electrode connector 120. This vertically-oriented mating surface of the first portion 126 includes two opposing side surfaces that are planar, and two opposing side surfaces that are curved. The first portion 126 further includes a horizontally-oriented mating surface at the base of the columnar portion 240. The first portion 126 is surrounded by the second portion 127, and the second portion 127 surrounds the first portion 126. The first portion 126 is also positioned closer to the distal end of the electrode connector 120 than the second portion 127.

The second portion 127 has a first planar surface 232 (sometimes referred to herein as an "upper surface") and a second planar surface 234 (sometimes referred to herein as a "lower surface") that are linked by a sloped surface 236 (or inclined surface 236) that is also planar, but inclined at an angle relative to imaginary transverse, midsagittal, and frontal planes of the electrode connector 120. Said another way, the first planar surface 232 and the second planar surface 234 are staggered in the sense that the first planar surface 232 is closer to the distal end of the electrode connector 120 (which includes the columnar portion 240 and is configured to be coupled to a cable 130 or medical device 140), and the second planar surface 234 is farther from the distal end of the electrode connector 120, and, hence, closer to the proximal end of the electrode connector 120 where the electrical cables 114a, 114b are coupled to the electrode connector 120. That is, the first planar surface 232 is a first distance from the distal end of the electrode connector 120, the second planar surface 234 is a second distance from the distal end of the electrode connector 120 (the second distance greater than the first distance), and the sloped surface 236 is between the first planar surface 232 and the second planar surface 234. The staggered surfaces 232, 234, and the sloped surface 236 act as a key, allowing the electrode connector 120 to couple to a cable 130 or medical device 140 having a complementary profile. Additionally, the surfaces 232, 234, and 236 of the second portion 127 ensure that the electrode connector 120 is oriented and aligned to properly couple to the cable 130 or medical device 140 so that the proper electrical connections or contacts are coupled together. That is, the profile of the second portion 127 allows the electrode connector 120 to couple to a corresponding cable 130 or medical device 140 in a particular orientation relative to the cable 130 or medical device 140, but if the electrode connector 120 is rotated 180 degrees about the longitudinal axis running from the proximal end to the distal end of the electrode connector 120, the profile of the second portion 127 would be oriented such that the electrode connector 120 cannot be coupled to the cable 130 or medical device 140, at least while the electrode connector 120 is in the improper orientation. In other words, the surfaces 232, 234, and 236 of the second portion 127 create a single orientation in which the electrode connector 120 is configured to be coupled to a corresponding receptacle of a cable 130 or medical device 140.

The columnar portion 240 of the electrode connector 120 includes a first column 242, a central column 244, and a second column 246. The columnar portion 240 is configured to couple to one or more complementary receptacles of the cable 130 or medical device 140 to which the electrode connector 120 is coupled. Electrical connections or contacts within the columnar portion 240 are configured to couple to electrical connections or contacts of the cable 130 or medical device 140 to establish an electrical connection between the electrode connector 120 and the cable 130 or medical device 140. In the example shown, the first and second columns 242, 246 include respective electrical contacts that are configured to carry an electrical signal, such as a defibrillation shock, transmitted from a defibrillation device (which is a type of medical device 140) to which the electrode connector 120 is coupled. The first column 242 is positioned at a first location adjacent to (e.g., within a threshold distance from, such as within a few millimeters from) the central column 244 and includes a first electrical connection (or contact) that is coupled to a first electrode 112a, and, hence, is configured to deliver a first electrical signal to the first electrode 112a, such as for delivering a defibrillation shock. The second column 246 is positioned at a second location adjacent to the central column 244 (on an opposing side of the central column 244 as the first column 242) and includes a second electrical connection (or contact) that is coupled to a second electrode 112b, and, hence, is configured to deliver a second electrical signal to the second electrode 112b, such as for delivering a defibrillation shock. In this manner, electrical signals, such as defibrillation shocks, are received by the electrode connector 120 from the coupled medical device 140 (e.g., defibrillator) and terminated at the electrodes 112 during operation. The central column 244 includes a third electrical connection(s) (or contact(s)) that is/are coupled to each of the electrodes 112a, 112b and that is/are used to deliver/transmit electrical signals from the patient to the coupled cable 130 or medical device 140 during operation. In this example, electrical contacts of the first and second columns 242, 246 are used to transmit electrical energy to the electrodes 112 and the electrical contact(s) of the central column 244 is/are used to transmit electrical energy, such as patient electrical activity, or data indicative of a physiological parameter (sensed physiological parameter data or information) of the patient, from the electrodes 112. Thus, the electrodes 112—when coupled to the medical device 140 (e.g., defibrillator), and when placed on a patient—are configured to both gather the patient physiological data of the patient and administer therapy to the patient, when warranted. For example, the medical device 140 (e.g., defibrillator), or a user thereof, evaluates the patient physiological data or information to determine whether to deliver therapy (e.g., defibrillation therapy) via the electrodes 112.

Figure 3:
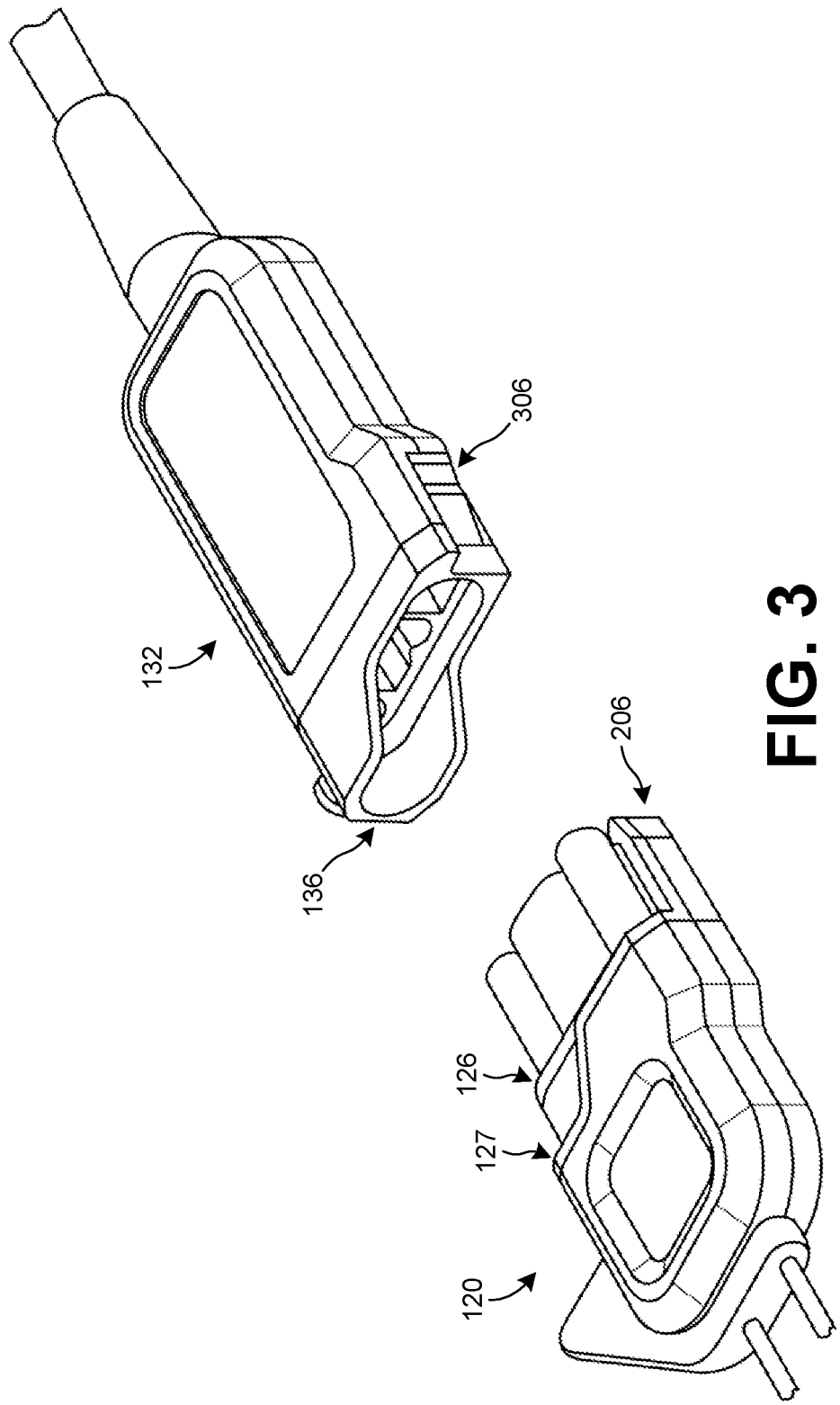
FIG. 3 illustrates the example electrode connector shown in FIGS. 2A and 2B coupled to an example electrical cable.

FIG. 3 illustrates an example electrode connector 120 being coupled to an example electrode receptacle 132 of an electrical cable 130. The electrode receptacle 132 of the electrical cable 130 includes a recess 306 defined on a side of the receptacle 132 for receiving the tab 206, or portion thereof, of the electrode connector 120. The electrode receptacle 132 of the electrical cable 130 further includes an interface 136 (sometimes referred to herein as an "engagement portion") for coupling to the second portion 127 of the electrode connector 120. Aligning and sliding the electrode connector 120 and electrode receptacle 132 of the cable 130 together causes the tab 206 to slide along an outer side portion of the electrode receptacle 132 until the protrusion of the tab 206 couples to the recess 306 defined in the side of the receptacle 132. The coupling of the protrusion of the tab 206 to the recess 306 causes an audible sound (e.g., "click"), which indicates to a user that the electrode connector 120 and electrode receptacle 132 of the cable 130 are properly and securely coupled. When the electrode connector 120 is coupled to the electrode receptacle 132 of the cable 130, electrical contacts of the electrode connector 120 are coupled to electrical contacts of the electrode receptacle 132 of the electrical cable 130 so that an electrical connection is formed between the electrodes 112 and the electrical cable 130, and the medical device 140 that is coupled to the other end of the electrical cable 130. The interface 136 of the electrode receptacle 132 of the electrical cable 130 is shaped and sized to be complementary to the second portion 127 of the electrode connector 120 to allow the electrode connector 120 and the electrode receptacle 132 to be coupled. However, while the electrode connector 120 includes portions 126, 127 to allow the electrode connector 120 to be compatible with both newer and older device versions, the electrode receptacle 132 of the electrical cable 130 is exclusively compatible with the electrode connector 120, or newer version electrodes 112, and is unable to receive older versions of electrode connectors. Alternatively, the electrode receptacle 132 of the electrical cable 130 includes similar reverse compatibility as the electrode connector 120 to allow older versions of electrode connectors to be coupled to the electrode receptacle 132 of the electrical cable 130.

FIGS. 4-7 illustrate example processes related to various implementations of the present disclosure. Although FIGS. 4-7 illustrate separate processes, in various examples, a single entity can perform any combination of the processes. Furthermore, although each of FIGS. 4-7 illustrates steps in a particular order, implementations are not limited to the specific order of operations illustrated in the figures.

Figure 4:
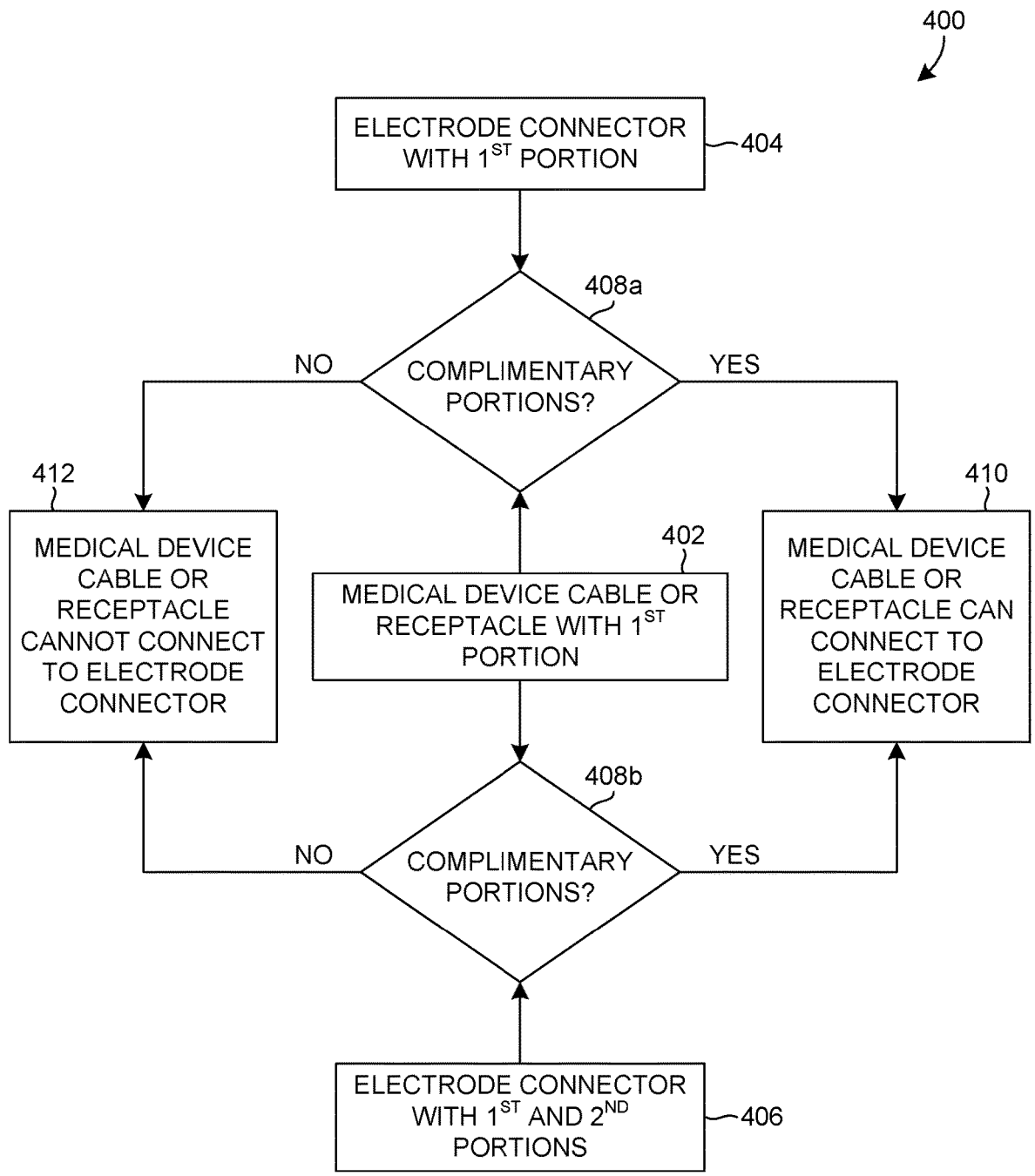
FIG. 4 illustrates an example process for coupling an electrode connector to an electrical cable or a receptacle of a medical device.

FIG. 4 illustrates an example process 400 for coupling an electrode connector to an electrical cable or a receptacle of a medical device to demonstrate the compatibility of electrode connectors and a medical device connector of an electrical cable 130 or receptacle of the medical device 140 itself. In the example, a user, at blocks 404 and 402, is attempting to couple a first electrode connector 120a having a first portion 126 (and possibly omitting a second portion 127) to an electrical cable 130 or a receptacle of a medical device 140 having a first portion. In the example, the electrical cable 130 or medical device 140 represents an older version that has the first portion. At a different time, the user, at blocks 406 and 402, is attempting to couple a second electrode connector 120b having a first portion 126 and a second portion 127 to the same, older version of electrical cable 130 or medical device 140.

At block 408a, if the first portion 126 of the first electrode connector 120a is complementary to the first portion of the electrical cable 130 or the receptacle of the medical device 140, then the electrical cable 130 or the receptacle of the medical device 140 connects to the first electrode connector 120a at block 410. If, at block 408a, the first portion 126 of the first electrode connector 120a is not complementary to the first portion of the electrical cable 130 or the receptacle of the medical device 140, then the electrical cable 130 or the receptacle of the medical device 140 does not (or is unable to) couple to the first electrode connector 120a at block 412.

Likewise, at block 408b, if one or both of the first portion 126 or the second portion 127 of the second electrode connector 120b is complementary to the first portion of the electrical cable 130 or the receptacle of the medical device 140, then the electrical cable 130 or the receptacle of the medical device 140 connects to the second electrode connector 120b at block 410. If, at block 408b, one or both of the first portion 126 or the second portion 127 of the second electrode connector 120b is not complementary to the first portion of the electrical cable 130 or the receptacle of the medical device 140, then the electrical cable 130 or the receptacle of the medical device 140 does not (or is unable to) couple to the second electrode connector 120b at block 412.

According to some examples, the first portion of the electrical cable 130 or the receptacle of the medical device 140 is complementary to the respective first portions 126 of both electrode connectors 120. In these examples, the first electrode connector 120a is an older version that is compatible with the older version of the electrical cable 130 or medical device 140 that has the first portion, while the second electrode connector 120b is a newer version that has reverse compatibility by virtue of including the first portion 126 to allow the second electrode connector 120b to be used with the older version of electrical cable 130 or medical device 140 that has the first portion. Accordingly, both electrode connectors 120 in the example of FIG. 4 are coupled at block 410, in an illustrative example.

Figure 5:
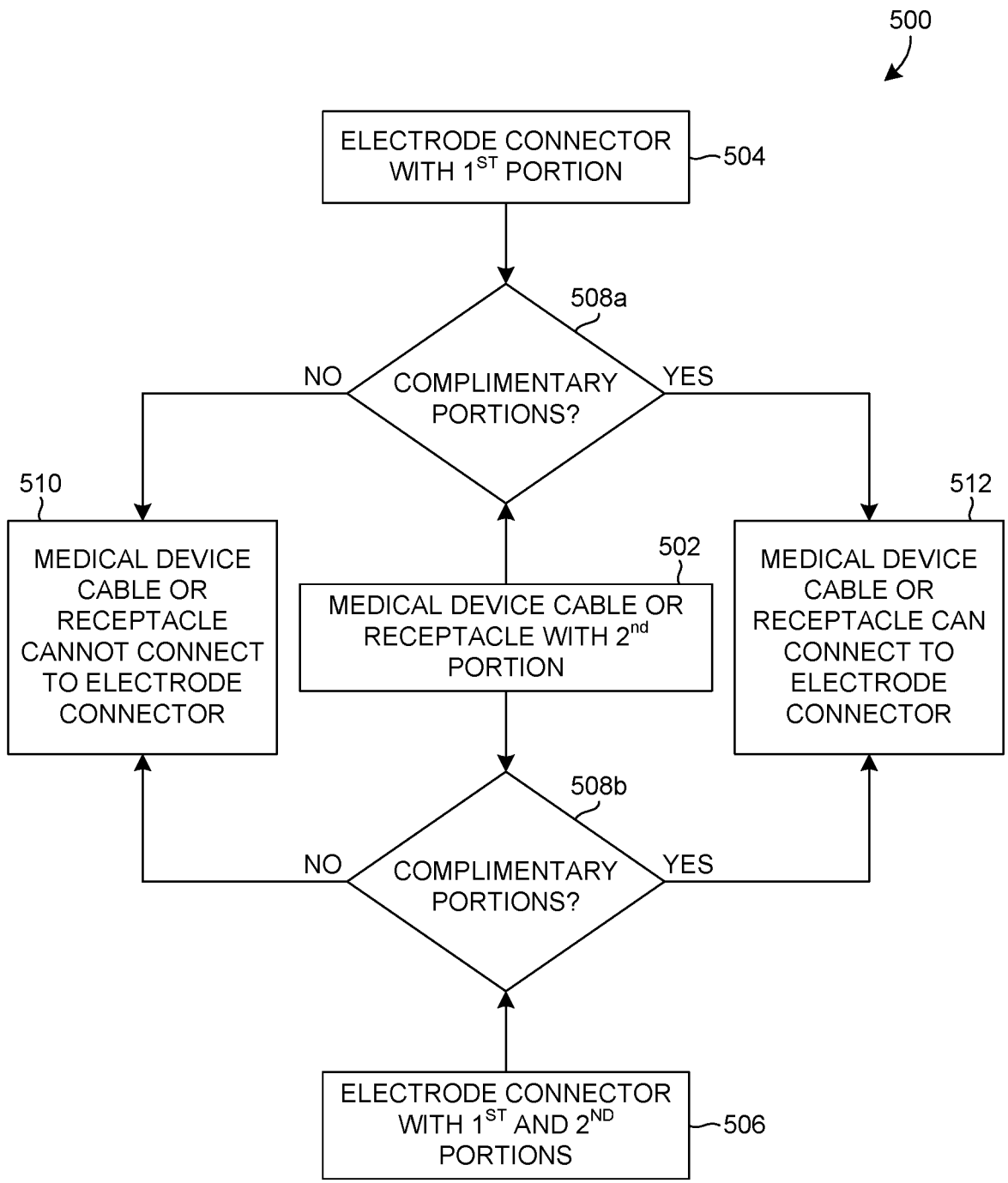
FIG. 5 illustrates another example process for coupling an electrode connector to an electrical cable or a receptacle of a medical device.

FIG. 5 illustrates another example process 500 for coupling an electrode connector to an electrical cable 130 or a receptacle of a medical device 140 to demonstrate the compatibility of electrode connectors and a medical device connector of an electrical cable 130 or receptacle of the medical device 140 itself. In the example, a user, at blocks 504 and 502, is attempting to couple a first electrode connector 120a having a first portion 126 (and possibly omitting a second portion 127) to an electrical cable 130 or a receptacle of a medical device 140 having a second portion. In the example, the electrical cable 130 or medical device 140 represents a newer version that has the second portion. At a different time, the user, at blocks 506 and 502, is attempting to couple a second electrode connector 120b having a first portion 126 and a second portion 127 to the same, newer version of electrical cable 130 or medical device 140.

At block 508a, if the first portion 126 of the first electrode connector 120a is complementary to the second portion of the electrical cable 130 or the receptacle of the medical device 140, then the electrical cable 130 or the receptacle of the medical device 140 connects to the first electrode connector 120a at block 512. If, at block 508a, the first portion 126 of the first electrode connector 120a is not complementary to the second portion of the electrical cable 130 or the receptacle of the medical device 140, then the electrical cable 130 or the receptacle of the medical device 140 does not (or is unable to) couple to the first electrode connector 120a at block 510.

Likewise, at block 508b, if one or both of the first portion 126 or the second portion 127 of the second electrode connector 120b is complementary to the second portion of the electrical cable 130 or the receptacle of the medical device 140, then the electrical cable 130 or the receptacle of the medical device 140 connects to the second electrode connector 120b at block 512. If, at block 508b, one or both of the first portion 126 or the second portion 127 of the second electrode connector 120b is not complementary to the second portion of the electrical cable 130 or the receptacle of the medical device 140, then the electrical cable 130 or the receptacle of the medical device 140 does not (or is unable to) couple to the second electrode connector 120b at block 510.

According to some examples, the second portion of the electrical cable 130 or the receptacle of the medical device 140 is not complementary to the respective first portions 126 of both electrode connectors 120. This means that the first electrode connector 120a and the electrical cable 130 or the receptacle of the medical device 140 do not have any complementary portions, and, hence, the electrical cable 130 or the receptacle of the medical device 140 does not couple (or is prevented from coupling) to the first electrode connector 120a at block 510. In these examples, the first electrode connector 120a is an older version that is incompatible with the newer version of the electrical cable 130 or medical device 140 that has the second portion. However, the second electrode connector 120b has the second portion 127, which is complementary to the second portion of the newer version electrical cable 130 or medical device 140. Thus, the electrical cable 130 or the receptacle of the medical device 140 connects to the second electrode connector 120b at block 512. In this manner, certain versions of electrode connectors 120 are prevented from coupling to certain electrical cables 130 or receptacles of medical devices 140 such as preventing older version electrode connectors from coupling to newer medical devices 140 or electrical cables 130. In an example, the newer version electrode connector 120b includes improved or additional features that the older version electrode connector 120a does not include, such as an authentication code 122 or memory 121. Older version electrode connectors lacking such a feature are prevented from coupling to newer version cables 130 and medical devices 140 that utilize such a feature, which is an enhanced safety feature.

Figure 6:
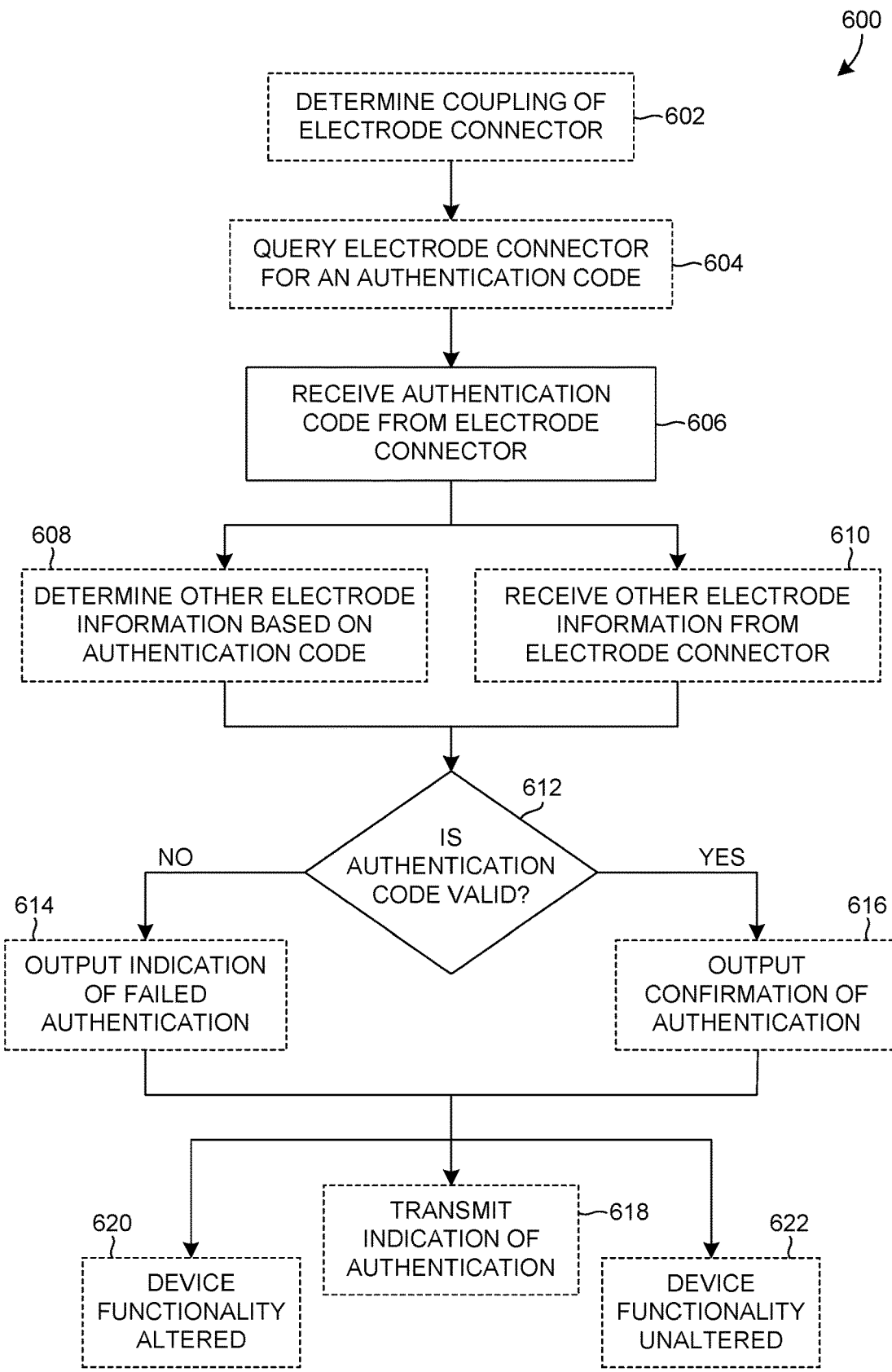
FIG. 6 illustrates an example process of authenticating electrodes.

FIG. 6 illustrates an example electrode authentication process 600. In various implementations, the process 600 is performed by an entity including the medical device 140 (e.g., a processor(s) of the medical device 140), a remote computing device or system, the electrode connector 120 (or a similar accessory), or any combination thereof.

At 602, a coupling of an electrode connector is determined. In an example, the electrode connector 120 is coupled to a cable 130 or to a medical device 140, and the medical device 140, at block 602, determines that the electrode connector 120 (or the electrodes 112) is/are coupled to the medical device 140. According to some examples, determining, at block 602, that the electrode connector 120 (or the electrodes 112) is/are coupled includes detecting an electrical connection between the electrodes 112 and the medical device 140. According to some examples, the electrode connector 120 determines, at block 602, that the medical device 140 is coupled to the electrode connector 120.

At 604, optionally, the electrode connector 120 is queried for an authentication code 122. In an example, the medical device 140 queries a memory 121 of the electrode connector 120 for the authentication code 122, such as when an electrical connection between the electrode connector 120 (or the electrodes 112) and the medical device 140 is established. In an example, the medical device 140 sends a query to the electrode connector 120 and the electrode connector 120 receives the query from the medical device 140. According to some examples, the authentication code 122 stored in the memory 121 of the electrode connector 120 is encrypted to maintain an integrity of the authentication code 122 and prevent unauthorized parties from accessing or receiving the authentication code 122.

At 606, the authentication code 122 is received from the electrode connector 120. In an example, in response to receiving the query at 604, the electrode connector 120 sends the authentication code 122 to the medical device 140, and the medical device 140 receives the authentication code 122 from the electrode connector 120. Alternatively, the medical device 140 is configured to access the memory 121 of the electrode connector 120 to retrieve the authentication code 122.

At 608 and 610, other information regarding the electrodes 112 is obtained. In an example, at 608, other information regarding the electrodes 112 is determined (e.g., by the medical device 140) based on the authentication code 122, such as by processing or parsing the authentication code 122 to determine the other information, as described herein. In another example, at 610, other information regarding the electrodes 112 is retrieved from the memory 121 of the electrode connector 120, such as using the same query at 604, a separate query(ies), or upon coupling of the electrode connector 120 to the medical device 140.

In an example, such as at 608, the authentication code 122 is associated (e.g., the authentication code 122 is structured to contain) additional information regarding the electrode 112, such as an expiration date of the electrodes 122, a type or model of the electrodes 112, and the like. In an example, the authentication code 122 is made up of a series of characters, a subset of which is the authenticating portion of the code 122 and another subset of characters is used to encode, or be representative of, other information regarding the electrodes 112, such as the expiration date or the electrode type.

According to some examples, the authentication code system or algorithm includes a time-based component, with one or more authentication codes 122 associated with a manufacturing or expiration date of the electrodes 112. In these examples, the medical device 140 receives the authentication code 122 from the electrode connector memory 121 and compares the authentication code 122 to a table or other database to determine a corresponding time component, such as an expiration or manufacturing date, associated with the authentication code 122, which, in turn, is associated with the electrodes 112 that are coupled to the electrode connector 120. In these examples, the medical device 140 then compares the determined time component information with the current date to determine if the electrodes 112 are expired or how much remaining life the electrodes 112 have until expiration.

In another example, such as at 610, the medical device 140 receives other information, such as an expiration date of the electrodes 112 or type of the electrodes 112, from the memory 121 of the electrode connector 120, such as upon the coupling of the electrode connector 120 to the medical device 140. In these examples, the other information regarding the electrodes 112 is stored within the memory 121 of the electrode connector 120 where the information is accessible, such as by reading, retrieving or receiving, by a medical device 140 coupled to the electrode connector 120.

At 612, the authentication code 122 is validated. Validating the authentication code 122 involves one or more processes, elements, or combination thereof. In an example, the authentication code 122 is validated by performing one or more mathematical operations to determine the validity of the authentication code 122. In another example, the validation is performed by comparing the authentication code 122 with a list of known and valid authentication codes 122, such as a list stored on the medical device 140. If the authentication code 122 received from the electrode connector 120 is on the list of know authentication codes, then the authentication code 122 is validated. According to some examples, the list of authentication codes maintained by the medical device 140 includes a time component indicating one or more authentication codes that are valid during a period of time. If the authentication code 122 received from the electrode connector 120 is on the list but is not currently valid, as indicated by the time component, then the authentication code 122 is not validated (or is determined to be invalid). Additionally, if no authentication code 122 is received from the electrode connector 120, the electrodes fail to be authenticated. According to some examples, such as where the authentication code 122 is associated with an expiration date of the electrodes 112, the expiration date is evaluated at block 612 for use in determining whether the electrodes 112 are expired or not. This may be factored into the determination to authenticate the electrodes 112. In an example, the authentication code 122 may be valid, but the electrodes 112 are nevertheless expired based on the expiration date. Alternatively, in some examples, the authentication code 122 is considered to be invalid based on an expiration date in the past.

If the electrode authentication code 122 is not validated at 612, then an indication of the failed authentication of the electrodes 112 (or the invalid authentication code 122) is output at 614 (e.g., output from the medical device 140). According to some examples, the indication is an audible output, a visual output, a vibratory output, or combination thereof, of the medical device 140 that indicates to a user that the coupled electrodes 112 failed to be authenticated. If the electrode authentication code 122 is validated at 612, then a confirmation of the authentication of the electrodes 112 (or the valid authentication code 122) is output at 616 (e.g., output from the medical device 140). According to some examples, the output at block 616 includes an audible output, a visual output, a vibratory output, or combination thereof, of the medical device 140 that indicates to a user that the electrodes coupled to the medical device 140 are authenticated. According to some examples, if the expiration date of the electrodes 112 is a date in the past, meaning that the electrodes 112 are expired, an indication of a failed authentication of the electrodes 112 is output at 614, regardless of whether the authentication code 122 itself is valid or invalid. According to some examples, determining that electrodes 112 are expired causes the authentication code 122 to be deemed invalid.

After the electrodes 112 are authenticated or not, an indication of the authentication of (or failure to authenticate) the electrodes 112 is transmitted at 618, functionality of a device is altered at 620, functionality of a device is unaltered at 622, or a combination(s) thereof. At 618, the indication of the authentication of (or failure to authenticate) the electrodes 112 is transmitted. In an example, the medical device 140 coupled to the electrode connector 120 transmits the indication of the authentication to a remote device or system, such as a user device, a medical device management system, or a system of a manufacturer of the medical device 140. Transmitting the indication of the authentication (or failure to authenticate) allows the use of authenticated and non-authenticated electrodes 112 to be tracked and monitored. According to some examples, non-authenticated electrodes 112 are manufactured by third parties not licensed by the medical device manufacturer to supply such an accessory. As such, the non-authenticated electrodes 112 lack oversight or have properties and characteristics that are not within the specifications or tolerances of the electrodes 112 of the medical device manufacture. Due to these differences, non-authenticated electrodes do not perform as desired during use with the medical device 140. The medical device manufacturer tracks the usage of non-authenticated electrodes for statistical or other purposes, such as to educate customers regarding the potential hazards of using non-authenticated electrodes with the medical device 140.

At 620, device functionality is altered, such as altering one or more functions or features of the medical device 140. In an example, the medical device 140 alters functionality, such as limiting or reducing one or more functions or features, in response to non-authenticated electrodes 112 being coupled thereto. According to some examples, the non-authenticated electrodes 112 have unknown properties or characteristics, which affects the quality of collected physiological parameter data using the non-authenticated electrodes 112. Due to the unknown quality of the physiological parameter data, analysis of such data by the medical device 140 has an increased margin of error or causes increased threshold levels to be used in the analysis to assist with increasing the accuracy of the analysis using the unknown quality of the physiological parameter data. According to some examples, other functions or features of the medical device 140 are similarly reduced or prevented from use, such as preventing the use of one or more functions or features of the medical device 140 when non-authenticated electrodes 1120 are coupled thereto. Alternatively, or additionally, based on the authentication of the coupled electrodes 112, functions or features of the medical device 140 are accessible or usable. According to some examples, a confidence in the accuracy of an analysis performed by the medical device 140 is increased due to the use of physiological parameter data collected using authenticated electrodes 112, which have known properties, characteristics or tolerances thereof. Similarly, thresholds used in the analysis to make determinations are refined due to the use of known-quality physiological parameter data acquired using the authenticated electrodes 112.

At 622, device functionality is unaltered in response to the authentication of (or failure to authenticate) the electrodes 112 coupled to the medical device 140. In an example, the medical device 140 maintains substantially similar functionality and features regardless of whether authenticated or non-authenticated electrodes 112 are coupled thereto. However, while the functionality and features of the medical device 140 remain substantially the same, the quality or accuracy of the functions and features of the medical device 140 are, in some examples, adversely effected due to the use of non-authenticated electrodes, which have unknown properties and characteristics.

Figure 7:
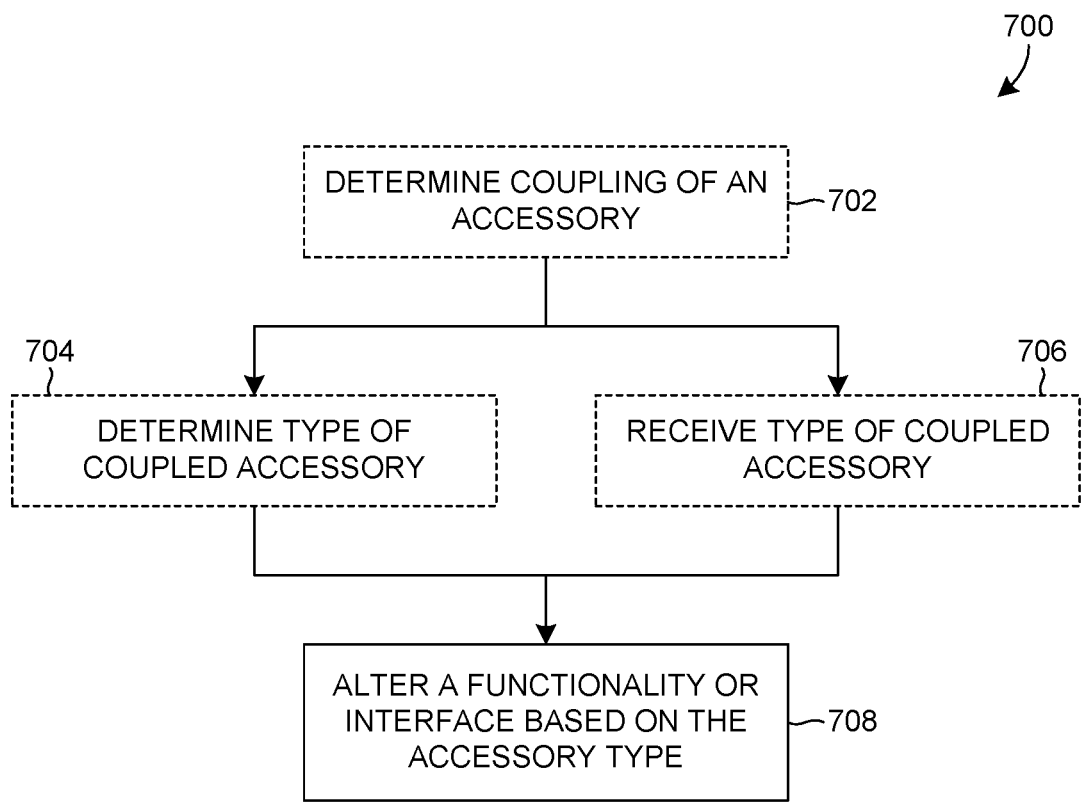
FIG. 7 illustrates an example process of altering the functionality of a medical device based on a type of a coupled accessory.

FIG. 7 is an example process 700 of altering a functionality or user interface based on a type of an accessory coupled to a medical device. In various implementations, the process 700 is performed by an entity including the medical device 140 (e.g., a processor(s) of the medical device 140)), a remote computing device or system, the electrode connector 120 (or a similar accessory), or any combination thereof.

At 702, the coupling of an accessory to the device is determined. In an example, the medical device 140 determines that an accessory has been coupled to the medical device 140, or the medical device 140 receives a user input indicating that an accessory has been coupled, such as by a user selection or input. In an example, the accessory is the electrodes 112.

At 704, the type of the coupled accessory is determined. For example, the medical device 140 has ports for various accessories and each of the ports is shaped to receive a specific accessory associated with the port. When an accessory is coupled to a port, the medical device 140 assumes or determines that the accessory is of a type associated with that port. In an illustrative example, coupling an electrocardiogram (ECG) accessory to an ECG port of the medical device 140 causes the medical device 140 to determine that the coupled accessory is associated with ECG data collection.

In another example, the medical device 140 determines an accessory is coupled to a port, such as by an electrical connection between the medical device and the accessory, and determines the accessory type based on the electrical connection. In yet another example, the accessory includes a memory or other storage media that contains an indication of the type of the accessory. When the accessory is coupled to the medical device 140, the medical device 140 obtains or reads the type of the accessory from the memory of the accessory, such as a type of electrodes 112 read from the memory 121 of the electrode connector 120.

At 706, the type of the accessory is received by the medical device 140. In an example, a user provides an input to the medical device 140 indicating the accessory type. In another example, the accessory transmits data or a signal indicative of its type to the medical device 140, and the medical device 140 receives the data or signal and determines the type of accessory therefrom.

At 708, a functionality or user interface of the medical device 140 is configured or altered based on the accessory type. According to some examples, configuring the functionality of the medical device 140 includes configuring the medical device 140 for operation with the accessory (e.g., electrodes 112) based on the type of the accessory (e.g., adjusting settings, parameters, etc.). In another example, a user interface or device option(s) of the medical device 140 is/are altered based on the type of the accessory. In an illustrative example, an electrode connector 120 for electrodes 112 is coupled to the medical device 140, and, based on the determined or received type of accessory, the medical device 140 presents, at block 708, a user interface for defibrillation or ECG functionality or features. In this manner, the medical device 140 at least partially configures itself for use based on the determined type of the coupled accessory. This increases efficiency of the use of the medical device 140 since a user in not required to provide one or more inputs to configure the medical device 140 for the type of coupled accessory.

Figure 8:
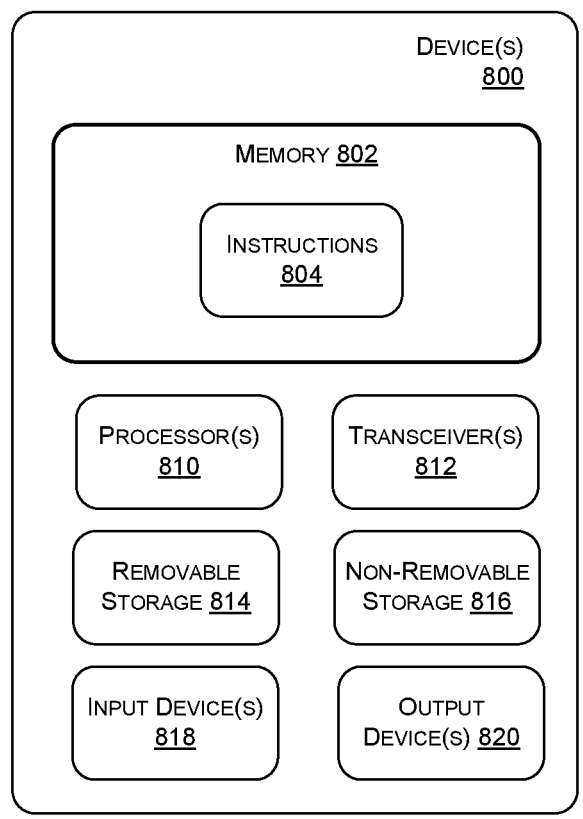
FIG. 8 illustrates an example computing system configured to perform the techniques described herein.

FIG. 8 illustrates an example computing system 800 including at least one device. In some implementations, the system 800 illustrated in FIG. 8 is configured to perform any of the functionality described herein. The system 800, in some examples, includes or represents the medical device 140 described herein. The system 800, in other examples, includes or represents the electrode connector 120 described herein. In some examples, the system 800 is implemented by at least one of server computer(s), dedicated hardware, software operating on dedicated hardware, or virtualized function(s) hosted on an appropriate platform (e.g., as cloud infrastructure). In some cases, the system 800 is implemented as a single device or as multiple devices with components and data distributed among them.

As illustrated, the system 800 includes a memory 802. In various implementations, the memory 802 is volatile (such as Random Access Memory (RAM)), non-volatile (such as Read Only Memory (ROM), flash memory, etc.) or some combination of the two. Various elements stored in the memory 802 include methods, threads, processes, applications, objects, modules, any other sort of executable instructions, or a combination thereof. Elements stored in the memory 802 may be non-transitory. The memory 802 stores various files, databases, or the like, in some cases.

The memory 802 includes various instructions 804, which are for executing any of the functionality described herein. For example, the memory 802 may store any of the modules or data described above with reference to FIG. 1.

In various examples, the instructions 804 are executed by processor(s) 810 to perform operations. In some embodiments, the processor(s) 810 includes a Central Processing Unit (CPU), a Graphics Processing Unit (GPU), or both CPU and GPU, or other processing unit or component known in the art.

As illustrated in FIG. 8, the system 800 also includes one or more wired or wireless transceiver(s) 812. For example, the transceiver(s) 812 include, for example, a Network Interface Card (NIC), a network adapter, a Local Area Network (LAN) adapter, or a physical, virtual, or logical address to connect to the various external devices and/or systems. In various examples, the transceiver(s) 812 include any sort of wireless transceivers capable of engaging in wireless communication (e.g., Radio Frequency (RF) communication). In some cases, the transceiver(s) 812 include other wireless modems, such as a modem for engaging in WI-FI®, WIGIG®, WIMAX®, BLUETOOTH®, or infrared communication. For example, the system 800 is configured to transmit and/or receive data with one or more external devices.

In some examples, the system 800 also includes additional data storage components such as, for example, magnetic disks, optical disks, or tape. These additional data storage components include removable storage 814 and non-removable storage 816. Tangible computer-readable media include volatile and nonvolatile, removable and non-removable media implemented in any method or technology for storage of information, such as computer readable instructions, data structures, program modules, or other data.

The memory 802, removable storage 814, and non-removable storage 816 are all examples of computer-readable storage media. Computer-readable storage media include RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the system 800. Any such tangible computer-readable media can be part of the 800. In various examples, any portion of the data described herein is/are stored in the memory 802, removeable storage 814, non-removable storage 816, or a combination thereof.

In various cases, the system 800 also includes input device(s) 818 and output device(s) 820. In some implementations, the input device(s) 820 includes at least one of a keypad, a cursor control, a touch-sensitive display, a voice input device, a haptic feedback device, or any combination thereof. According to some implementations, the input device(s) 818 are configured to receive one or more user input signals. In some cases, the input device(s) 818 include one or more physiological parameter sensors, such as electrodes 112. According to some example, the output device(s) 820 include at least one of a display, speakers, a haptic output device, printers, electrodes 112, etc. In some implementations, the input device(s) 818 include one or more touch sensors, the output device(s) 820 include a display screen, and the touch sensor(s) are integrated with the display screen. Thus, in some cases, the system 800 includes a touchscreen configured to receive user input signal(s) and visually output information.

Example Clauses

1. A system including: a first electrical cable including a first end and a second end; a second electrical cable including a first end and a second end; a set of electrodes including: a first electrode coupled to the first end of the first electrical cable; and a second electrode coupled to the first end of the second electrical cable; and an electrode connector coupled to the second end of the first electrical cable and to the second end of the second electrical cable the electrode connector including: a housing including: a first portion shaped to mate with a first receptacle of a first version of the medical device; and a second portion shaped to mate with a second receptacle of a second version of the medical device, the second receptacle different than the first receptacle; and memory storing an authentication code, wherein, upon coupling of the electrode connector to the second version of the medical device via the second receptacle, the memory is configured to permit the second version of the medical device to access the authentication code for use in authenticating the set of electrodes.

2. The system of clause 1, wherein: the first portion of the housing has an oblong-shaped cross-section with rounded ends; and the second portion of the housing surrounds the first portion of the housing.

3. The system of clause 1 or 2, wherein the second portion of the housing includes: a first planar surface that is a first distance from a distal end of the electrode connector; a second planar surface that is a second distance from the distal end of the electrode connector, the second distance greater than the first distance; and a sloped surface between the first planar surface and the second planar surface.

4. The system of any one of clauses 1 to 3, wherein the electrode connector further includes: a first column positioned at a first location adjacent to a central column, the first column including a first electrical contact configured to deliver a first electrical signal to the first electrode; a second column positioned at a second location adjacent to the central column, the second column including a second electrical contact configured to deliver a second electrical signal to the second electrode; and the central column including a third electrical contact configured to deliver, to the second version of the medical device, data indicative of a physiological parameter of a patient.

5. The system of any one of clauses 1 to 4, wherein the memory is further configured to store data received from the second version of the medical device, the data associated with a session in which the set of electrodes was used to treat a patient.

6. The system of any one of clauses 1 to 5, the memory further storing an expiration date of the set of electrodes, wherein, upon the coupling of the electrode connector to the second version of the medical device, the memory is configured to permit the second version of the medical device to access the expiration date for use in determining whether the set of electrodes is expired.

7. The system of any one of clauses 1 to 6, the memory further storing a type of the set of electrodes, wherein, upon the coupling of the electrode connector to the second version of the medical device, the memory is configured to permit the second version of the medical device to access the type of the set of electrodes for use in configuring the second version of the medical device for operation with the set of electrodes.

8. A system including: a set of electrodes; and an electrode connector coupled to the set of electrodes by a set of electrical cables, the electrode connector configured to be coupled to different versions of a medical device, to receive electrical signals generated by the medical device, and to terminate the electrical signals at the set of electrodes, the electrode connector including: a memory storing an authentication code; and a housing including: a first portion shaped to facilitate coupling of the electrode connector to a first version of the medical device; and a second portion shaped to facilitate coupling of the electrode connector to a second version of the medical device; wherein the electrode connector is configured to provide the medical device with access to the authentication code for validation of the authentication code.

9. The system of clause 8, wherein the electrode connector is configured to receive a query from the medical device, and to provide the authentication code to the medical device in response to receiving the query.

10. The system of clause 8 or 9, wherein the authentication code is associated with an expiration date of the set of electrodes, the expiration date for use by the medical device in determining whether the set of electrodes is expired.

11. The system of any one of clauses 8 to 10, wherein the authentication code is associated with a type of the set of electrodes for use by the medical device in configuring a functionality of the medical device.

12. The system of any one of clauses 8 to 11, wherein the medical device is a defibrillator, and wherein the electrical signals deliver one or more defibrillation shocks via the set of electrodes.

13. The system of any one of clauses 8 to 12, wherein: the first portion of the housing has an oblong-shaped cross-section with rounded ends; and the second portion of the housing surrounds the first portion of the housing.

14. The system of any one of clauses 8 to 13, wherein the second portion of the housing includes: a first planar surface that is a first distance from a distal end of the electrode connector; a second planar surface that is a second distance from the distal end of the electrode connector, the second distance greater than the first distance; and a sloped surface between the first planar surface and the second planar surface.

15. The system of any one of clauses 8 to 14, wherein the electrode connector further includes: a first column positioned at a first location adjacent to a central column, the first column including a first electrical connection configured to deliver a first electrical signal of the electrical signals to the first electrode; and a second column positioned at a second location adjacent to the central column, the second column including a second electrical connection configured to deliver a second electrical signal of the electrical signals to the second electrode.

16. A system including: a set of electrodes; and an electrode connector coupled to the set of electrodes by a set of electrical cables, the electrode connector configured to be coupled to different versions of a medical device, the electrode connector including: a memory storing an authentication code; and a housing including: a first portion having a first shape to facilitate coupling of the electrode connector to a first version of the medical device; and a second portion having a second shape to facilitate coupling of the electrode connector to a second version of the medical device; wherein the electrode connector is configured to provide the medical device with access to the authentication code for use in authenticating the set of electrodes for use with the medical device.

17. The system of clause 16, wherein: the first portion of the housing has an oblong-shaped cross-section with rounded ends; and the second portion of the housing surrounds the first portion of the housing.

18. The system of clause 16 or 17, wherein the second portion of the housing includes: a first planar surface that is a first distance from a distal end of the electrode connector; a second planar surface that is a second distance from the distal end of the electrode connector, the second distance greater than the first distance; and a sloped surface between the first planar surface and the second planar surface.

19. The system of any one of clauses 16 to 18, wherein the authentication code is associated with an expiration date of the set of electrodes, the expiration date for use by the medical device in determining whether the set of electrodes is expired.

20. The system of any one of clauses 16 to 19, wherein the authentication code is associated with a type of the set of electrodes for use by the medical device in configuring a functionality of the medical device.

21. A method including: determining that an electrode connector has been coupled to a medical device, the electrode connector coupled to a set of electrodes by a set of electrical cables and including a housing including a first portion shaped to facilitate coupling of the electrode connector to a different medical device that differs from the medical device by version, and a second portion shaped to facilitate coupling of the electrode connector to the medical device; and providing, based at least in part on the determining that the electrode connector has been coupled to the medical device, the medical device with access to an authentication code stored in memory of the electrode connector for validation of the authentication code.

22. The method of clause 21, further including: receiving electrical signals generated by the medical device; and terminating the electrical signals at the set of electrodes.

23. The method of clause 21 or 22, wherein the providing includes receiving a query from the medical device, and transmitting the authentication code to the medical device in response to the receiving of the query.

24. The method of any one of clauses 21 to 23, further including: receiving, from the medical device, data associated with a session in which the set of electrodes was used to treat a patient; and storing the data in the memory.

25. One or more non-transitory computer-readable media storing computer-executable instructions that, when executed by a processor, cause the processor to: determine that an electrode connector has been coupled to a medical device, the electrode connector coupled to a set of electrodes by a set of electrical cables and including a housing including a first portion shaped to facilitate coupling of the electrode connector to a different version of the medical device, and a second portion shaped to facilitate coupling of the electrode connector to the medical device; and provide, based at least in part on the determining that the electrode connector has been coupled to the medical device, the medical device with access to an authentication code stored in memory of the electrode connector for validation of the authentication code.

26. The one or more non-transitory computer-readable media of clause 25, wherein providing the medical device with access to the authentication code includes receiving a query from the medical device, and transmitting the authentication code to the medical device in response to the receiving of the query.

27. The one or more non-transitory computer-readable media of clause 25 or 26, wherein the computer-executable instructions, when executed by the processor, further cause the processor to: receive, from the medical device, data associated with a session in which the set of electrodes was used to treat a patient; and store the data in the memory.

28. A therapy electrode system including: an electrical cable having a first end and a second end; an electrode attached to the first end of the electrical cable; an electrical connector attached to the second end of the electrical cable and configured to receive an electrical signal from a medical device and to terminate the electrical signal at the electrode, the electrical connector having: a housing with a mating surface, the mating surface having a first portion and second portion, the first portion shaped to mate with a first portion of a first medical device receptacle and a first portion of a second medical device receptacle; the second portion shaped to mate with a second portion of the first medical device receptacle and shaped to prevent mating of the housing with a second portion of the second medical device receptacle; a memory electrically coupled to the electrical connector, the memory having an authentication code corresponding to one or more characteristics of one or both of the electrode and the electrical connector, wherein, upon coupling of the first portion and the second portion of the electrical connector to the respective first portion and second portion of the first medical device receptacle, the memory is configured to: permit interpretation of the authentication code by the medical device to confirm the authentication code to the medical device, and generate an output that confirms the authentication code.

29. The therapy electrode system of clause 28, wherein the electrical connector includes a first outer column and a second outer column arranged about a central column and at least one of the first outer column and the second outer column includes an electrical connection electrically connected to the electrode and the central column includes an electrical connection configured to exchange data with the medical device.

30. The therapy electrode system of clause 28 or 29, wherein the memory is configured to receive and store treatment session data from the medical device.

31. The therapy electrode system of any one of clauses 28 to 30, wherein the memory is configured to store an expiration date of the electrode, the expiration data retrievable by the medical device.

32. The therapy electrode system of any one of clauses 28 to 31, wherein the memory is configured to store a type of the electrode, the type retrievable by the medical device.

33. The therapy electrode system of any one of clauses 28 to 32, wherein the authentication code includes at least an indication of an expiration date of the electrode.

34. A therapy electrode system including: a first medical device cable having a first medical device connector attached to one end and an electrical connection configured to electrically couple to a port of a medical device on the other end, the first medical device cable configured to receive an electrical signal from the medical device; an electrode cable having an electrode attached at one end and an electrode connector attached at the other end, the electrode connector configured to receive the electrical signal from the medical device cable and to terminate the electrical signal at the electrode, the electrode connector having: a memory configured to store an authentication code associated with the medical device, the authentication code corresponding to one or more characteristics of one or both of the electrode cable and the electrode, and a housing and multiple electrical connections, the housing having a mating surface with a first portion and second portion, the first portion shaped to mate with a first portion of the first medical device connector and a first portion of a second medical device connector of a second medical device cable; the second portion shaped to mate with a second portion of the first medical device connector and shaped to prevent mating of the housing with a second portion of the second medical device connector of the second medical device; a processor configured to: upon mating of the housing of the electrode connector to the first medical device connector and the coupling of the multiple electrical connections of the electrode connector with the respective electrical connectors in the first medical device connector, query the memory for the authentication code, interpret the authentication code to confirm the authentication code to the medical device, and generate an output that confirms the authentication code.

35. The therapy electrode system of clause 34, wherein the one or more characteristics of one or both of the electrode cable and the electrode includes an expiration date.

36. The therapy electrode system of clause 34 or 35, wherein the output includes an indication of the expiration date.

37. The therapy electrode system of any one of clauses 34 to 36, wherein the processor is further configured to cause an alteration to one or more functionalities of the medical device based on the expiration date.

38. The therapy electrode system of any one of clauses 34 to 37, wherein the one or more characteristics of one or both of the electrode cable and the electrode includes an electrode type.

39. The therapy electrode system of any one of clauses 34 to 38, wherein the processor is further configured to cause an alteration to one or more functionalities of the medical device based on the electrode type.

40. The therapy electrode system of any one of clauses 34 to 39, wherein the authentication code includes an indication of an expiration date of the electrode and wherein the processor is further configured to determine the expiration date of the electrode from the authentication code.

41. The therapy electrode system of any one of clauses 34 to 40, wherein the authentication code includes an indication of a type of the electrode and wherein the processor is further configured to determine the type of the electrode from the authentication code.

42. The therapy electrode system of any one of clauses 34 to 41, wherein the processor is further configured to cause the output to be transmitted to at least one of a remote device or remote system.

43. The therapy electrode system of any one of clauses 34 to 42, wherein the processor is further configured to cause an alteration to one or more functionalities of the medical device based on the confirmation of the authentication code.

44. A therapy electrode system including: an electrical cable having a first end and a second end; an electrode attached to the first end of the electrical cable, the electrode having an electrical property; an electrical connector attached to the second end of the electrical cable and configured to receive an electrical signal from a medical device and to terminate the electrical signal at the electrode; a processor configured to generate instructions to: upon coupling of the electrode connector to the medical device, detect a value of the electrical property of the electrode; identify the electrode as authentic if the value of the electrical property of the coupled electrode is detected to be within a range of values of the electrical property of the electrode; and output data that indicates that the electrode is authentic to a diagnostic circuit configured to diagnose a patient, wherein the electrode is a component of the circuit.

45. The therapy electrode system of clause 44, further including a diagnostic algorithm configured to: receive a value of a patient physiological parameter, receive the value of the electrical property of the electrode, and determine the diagnosis of the patient based on the patient physiological parameter and the value of the electrical property of the electrode.

46. A therapy electrode system including: an electrical cable having a first end and a second end; an electrode attached to the first end of the electrical cable, the electrode having an electrical property; an electrical connector attached to the second end of the electrical cable and configured to receive an electrical signal from a medical device and to terminate the electrical signal at the electrode; a processor configured to generate instructions to: upon coupling of the electrode connector to the medical device, detect a value of the electrical property of the electrode; determine if the value of the electrical property of the coupled electrode is outside of a range of values of the electrical property; and generate an instruction to alter functionality of one or both of a diagnostic algorithm and the medical device based on the determination that the value of the electrical property of the coupled electrode is outside of the range of values of the electrical property of the electrode.

47. A therapy electrode system including: an electrical cable having a first end and a second end; an electrode attached to the first end of the electrical cable, the electrode having an electrical condition; an electrical connector attached to the second end of the electrical cable and configured to receive an electrical signal from a medical device and to terminate the electrical signal at the electrode; a processor configured to generate instructions to: upon coupling of the electrode connector to the medical device, detect the electrical condition of the electrode; detect a value of the electrical condition of the coupled electrode; determine whether the electrode is authentic or non-authentic based on whether the value of the electrical condition of the coupled electrode is determined to be respectively within or outside of a range of values of the electrical property of the electrode; and output data that indicates that the electrode is authentic or non-authentic to a diagnostic circuit configured to diagnose a patient, wherein the electrode is a component of the circuit.

48. A system including: an electrical cable including a first end and a second end; an electrode coupled to the first end of the electrical cable; an electrode connector coupled to the second end of the electrical cable and configured to receive an electrical signal from a medical device and to terminate the electrical signal at the electrode; and a processor configured to execute instructions to, upon coupling of the electrode connector to the medical device: detect a value of an electrical property of the electrode; identify the electrode as authentic based at least in part on the value of the electrical property being within a range of values; and output, to a circuit configured to diagnose a patient, data that indicates the electrode is authentic, wherein the electrode is a component of the circuit.

49. A method including: detecting, by a processor of a medical device coupled to an electrode connector, a value of an electrical property of an electrode coupled to the electrode connector; identifying the electrode as authentic based at least in part on the value of the electrical property being within a range of values; and outputting, to a circuit configured to diagnose a patient, data that indicates the electrode is authentic, wherein the electrode is a component of the circuit.

50. One or more non-transitory computer-readable media storing computer-executable instructions that, when executed by a processor, cause the processor to: detect a value of an electrical property of an electrode coupled to an electrode connector; identify the electrode as authentic based at least in part on the value of the electrical property being within a range of values; and output, to a circuit configured to diagnose a patient, data that indicates the electrode is authentic, wherein the electrode is a component of the circuit.

51. A system including: an electrical cable including a first end and a second end; an electrode coupled to the first end of the electrical cable; an electrode connector coupled to the second end of the electrical cable and configured to receive an electrical signal from a medical device and to terminate the electrical signal at the electrode; and a processor configured to execute instructions to, upon coupling of the electrode connector to the medical device: detect a value of an electrical condition of the electrode; determine that the value of the electrical condition is within a range of values; and output, to a circuit configured to diagnose a patient, data that indicates the electrode is authentic based at least in part on the value of the electrical condition being within the range of values, wherein the electrode is a component of the circuit.

52. A method including: detecting, by a processor of a medical device coupled to an electrode connector, a value of an electrical condition of an electrode coupled to the electrode connector; determining that the value of the electrical condition is within a range of values; and outputting, to a circuit configured to diagnose a patient, data that indicates the electrode is authentic based at least in part on the value of the electrical condition being within the range of values, wherein the electrode is a component of the circuit.

53. One or more non-transitory computer-readable media storing computer-executable instructions that, when executed by a processor, cause the processor to: detect a value of an electrical condition of an electrode coupled to an electrode connector; determine that the value of the electrical condition is within a range of values; and output, to a circuit configured to diagnose a patient, data that indicates the electrode is authentic based at least in part on the value of the electrical condition being within the range of values, wherein the electrode is a component of the circuit.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the disclosed techniques and systems in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

The invention claimed is:

1. A system comprising:
a first electrical cable comprising a first end and a second end;
a second electrical cable comprising a first end and a second end;
a set of electrodes comprising:
a first electrode coupled to the first end of the first electrical cable; and
a second electrode coupled to the first end of the second electrical cable; and
an electrode connector coupled to the second end of the first electrical cable and to the second end of the second electrical cable, the electrode connector comprising:
a housing comprising:
a first portion having an oblong-shaped cross-section with rounded ends to mate with a first receptacle of a first version of a medical device; and
a second portion that surrounds the first portion of the housing, the second portion shaped to mate with a second receptacle of a second version of the medical device, the second receptacle different than the first receptacle; and
memory storing an authentication code, wherein, upon coupling of the electrode connector to the second version of the medical device via the second receptacle, the memory is configured to permit the second version of the medical device to access the authentication code for use in authenticating the set of electrodes.

2. The system of claim 1, wherein the second portion of the housing comprises:
a first planar surface that is a first distance from a distal end of the electrode connector;
a second planar surface that is a second distance from the distal end of the electrode connector, the second distance greater than the first distance; and
a sloped surface between the first planar surface and the second planar surface.

3. The system of claim 1, wherein the electrode connector further comprises:
a first column positioned at a first location adjacent to a central column, the first column comprising a first electrical contact configured to deliver a first electrical signal to the first electrode;
a second column positioned at a second location adjacent to the central column, the second column comprising a second electrical contact configured to deliver a second electrical signal to the second electrode; and
the central column comprising a third electrical contact configured to deliver, to the second version of the medical device, data indicative of a physiological parameter of a patient.

4. The system of claim 1, wherein the memory is further configured to store data received from the second version of the medical device, the data associated with a session in which the set of electrodes was used to treat a patient.

5. The system of claim 1, the memory further storing an expiration date of the set of electrodes, wherein, upon the coupling of the electrode connector to the second version of the medical device, the memory is configured to permit the second version of the medical device to access the expiration date for use in determining whether the set of electrodes is expired.

6. The system of claim 1, the memory further storing a type of the set of electrodes, wherein, upon the coupling of the electrode connector to the second version of the medical device, the memory is configured to permit the second version of the medical device to access the type of the set of electrodes for use in configuring the second version of the medical device for operation with the set of electrodes.

7. The system of claim 1, wherein the authentication code is associated with a type of the set of electrodes for use by the second version of the medical device in configuring a functionality of the second version of the medical device.

8. A system comprising:
a set of electrodes; and
an electrode connector coupled to the set of electrodes by a set of electrical cables, the electrode connector configured to be coupled to different versions of a medical device, to receive electrical signals generated by the medical device, and to terminate the electrical signals at the set of electrodes, the electrode connector comprising:
  a memory storing an authentication code, wherein the authentication code is associated with a type of the set of electrodes for use by the medical device in configuring a functionality of the medical device; and
  a housing comprising:
    a first portion shaped to facilitate coupling of the electrode connector to a first version of the medical device; and
    a second portion shaped to facilitate coupling of the electrode connector to a second version of the medical device;
  wherein the electrode connector is configured to provide the medical device with access to the authentication code for validation of the authentication code.

9. The system of claim 8, wherein the electrode connector is configured to receive a query from the medical device, and to provide the authentication code to the medical device in response to receiving the query.

10. The system of claim 8, wherein the authentication code is associated with an expiration date of the set of electrodes, the expiration date for use by the medical device in determining whether the set of electrodes is expired.

11. The system of claim 8, wherein the medical device is a defibrillator, and wherein the electrical signals deliver one or more defibrillation shocks via the set of electrodes.

12. The system of claim 8, wherein:
  the first portion of the housing has an oblong-shaped cross-section with rounded ends; and
  the second portion of the housing surrounds the first portion of the housing.

13. The system of claim 8, wherein the second portion of the housing comprises:
  a first planar surface that is a first distance from a distal end of the electrode connector;
  a second planar surface that is a second distance from the distal end of the electrode connector, the second distance greater than the first distance; and
  a sloped surface between the first planar surface and the second planar surface.

14. The system of claim 8, wherein the electrode connector further comprises:
  a first column positioned at a first location adjacent to a central column, the first column comprising a first electrical connection configured to deliver a first electrical signal of the electrical signals to a first electrode of the set of electrodes; and
  a second column positioned at a second location adjacent to the central column, the second column comprising a second electrical connection configured to deliver a second electrical signal of the electrical signals to a second electrode of the set of electrodes.

15. A method comprising:
determining that an electrode connector has been coupled to a medical device, the electrode connector coupled to a set of electrodes by a set of electrical cables and comprising a housing including a first portion shaped to facilitate coupling of the electrode connector to a different medical device that differs from the medical device by version, and a second portion shaped to facilitate coupling of the electrode connector to the medical device;
providing, based at least in part on the determining that the electrode connector has been coupled to the medical device, the medical device with access to an authentication code stored in memory of the electrode connector for validation of the authentication code;
receiving, from the medical device, data associated with a session in which the set of electrodes was used to treat a patient; and
storing the data in the memory.

16. The method of claim 15, further comprising:
receiving electrical signals generated by the medical device; and
terminating the electrical signals at the set of electrodes.

17. The method of claim 15, wherein the providing comprises:
receiving a query from the medical device; and
transmitting the authentication code to the medical device in response to the receiving of the query.

18. The method of claim 15, wherein the authentication code is associated with an expiration date of the set of electrodes, the expiration date for use by the medical device in determining whether the set of electrodes is expired.

19. The method of claim 15, wherein:
  the first portion of the housing has an oblong-shaped cross-section with rounded ends; and
  the second portion of the housing surrounds the first portion of the housing.

20. The method of claim 15, wherein the authentication code is associated with a type of the set of electrodes for use by the medical device in configuring a functionality of the medical device.

* * * * *